United States Patent [19]
Ladd et al.

[11] Patent Number: 5,584,830
[45] Date of Patent: Dec. 17, 1996

[54] METHOD AND SYSTEM FOR RADIOFREQUENCY ABLATION OF CARDIAC TISSUE

[75] Inventors: Kevin C. Ladd, Redwood City; Clifford C. Cox, San Jose, both of Calif.

[73] Assignee: Medtronic Cardiorhythm, San Jose, Calif.

[21] Appl. No.: 220,135

[22] Filed: Mar. 30, 1994

[51] Int. Cl.$^6$ .............................. A61B 17/39; A61N 1/05
[52] U.S. Cl. .................................. 606/34; 606/31; 606/41; 128/736; 607/99; 607/122
[58] Field of Search ..................................... 607/101, 102, 607/122, 98, 99; 606/42, 41, 49, 31, 34, 40; 128/736

[56] References Cited

U.S. PATENT DOCUMENTS

| | | | |
|---|---|---|---|
| 1,935,289 | 11/1933 | Evans | 175/294 |
| 3,588,710 | 6/1971 | Masters | 328/133 |
| 3,601,126 | 8/1971 | Estes | 128/303.14 |
| 3,785,383 | 1/1974 | Dotto | 128/414 |
| 3,800,802 | 4/1974 | Berry et al. | 128/422 |
| 4,196,734 | 4/1980 | Harris | 128/303.1 |
| 4,204,549 | 5/1980 | Paglione | 128/784 |
| 4,352,156 | 9/1982 | Gyugyi | 363/163 |
| 4,494,539 | 1/1985 | Zenitani et al. | 128/303.1 |
| 4,580,557 | 4/1986 | Hertzmann | 128/303.1 |
| 4,590,934 | 5/1986 | Malis et al. | 128/303.14 |
| 4,599,553 | 7/1986 | Brennen et al. | 323/205 |
| 4,632,127 | 12/1986 | Sterzer | 128/804 |
| 4,658,819 | 4/1987 | Harris et al. | 128/303.13 |
| 4,692,685 | 9/1987 | Blaze | 324/61 |
| 4,716,897 | 1/1988 | Noguchi et al. | 128/303.15 |
| 4,727,874 | 3/1988 | Bowers et al. | 128/303.13 |
| 4,739,759 | 4/1988 | Rexroth et al. | 128/303.14 |
| 4,805,621 | 2/1989 | Heinze et al. | 128/419 |
| 4,862,889 | 9/1989 | Feucht | 128/303.13 |
| 4,878,493 | 11/1989 | Pasternak et al. | 128/303.14 |
| 4,907,589 | 3/1990 | Cosman | 606/34 |
| 4,945,912 | 8/1990 | Langberg | 128/642 |
| 4,960,134 | 10/1990 | Webster, Jr. | 128/786 |
| 4,966,597 | 10/1990 | Cosman | 606/50 |
| 5,025,810 | 6/1991 | Kikuchi et al. | 607/102 |
| 5,122,137 | 6/1992 | Lennox | 606/40 |
| 5,167,660 | 12/1992 | Altendorf | 606/40 |
| 5,222,953 | 6/1993 | Dowlatshahi | 606/042 |
| 5,318,563 | 6/1994 | Malis et al. | 606/38 |
| 5,334,193 | 8/1994 | Nardella | 607/122 |

FOREIGN PATENT DOCUMENTS

| | | |
|---|---|---|
| 0136855 | 4/1985 | European Pat. Off. . |
| 0368532 | 5/1990 | European Pat. Off. . |
| 2164473 | 3/1986 | United Kingdom . |
| WO91/03208 | 3/1991 | WIPO . |
| WO91/16859 | 11/1991 | WIPO . |
| WO93/08756 | 5/1993 | WIPO . |
| WO93/08757 | 5/1993 | WIPO . |

*Primary Examiner*—Lee S. Cohen
*Attorney, Agent, or Firm*—Townsend and Townsend and Crew LLP

[57] ABSTRACT

A system for checking the initial calibration of a temperature measuring device that provides a temperature measuring signal in a catheter includes a comparison unit for comparing the magnitude of the temperature signal to a reference value indicating the normal body temperature of the patient. The treatment procedure is disabled if the magnitude of the temperature signal is not within a predetermined range of the reference value.

3 Claims, 30 Drawing Sheets

| FIG. 7A. | FIG. 7B. | FIG. 7C. |
| FIG. 7D. | FIG. 7E. | FIG. 7F. |

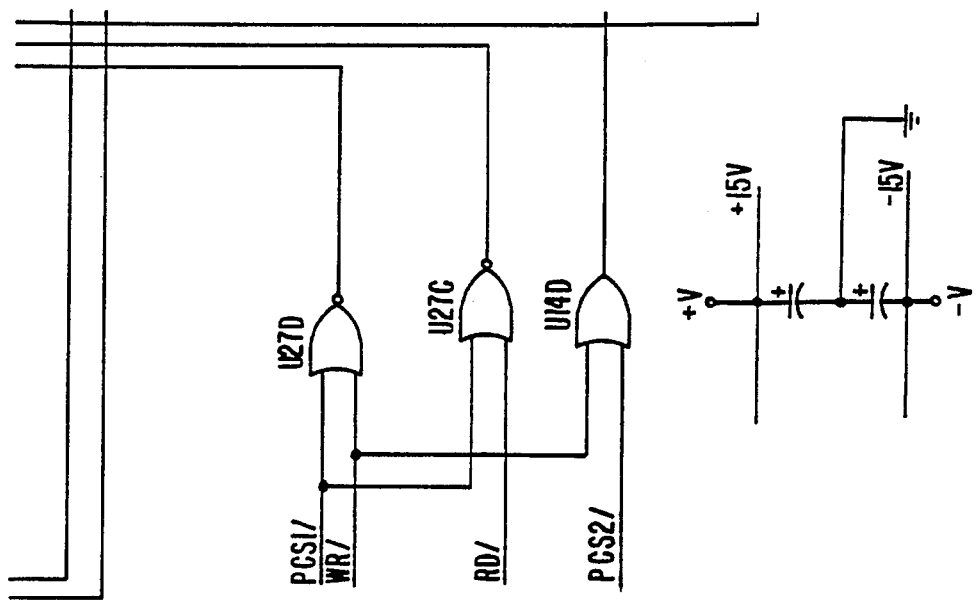
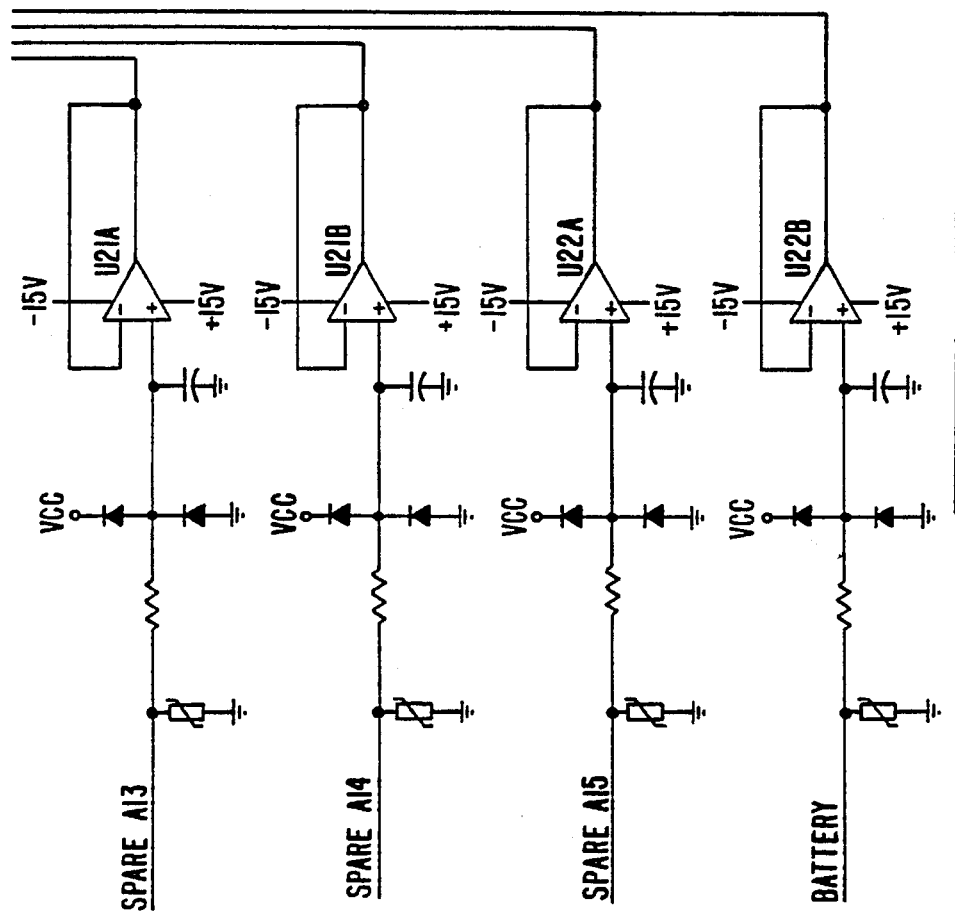
FIG. 9C.
FIG. 9.
| FIG. 9A. | FIG. 9B. |
| --- | --- |
| FIG. 9C. | FIG. 9D. |

| FIG. 10A. | FIG. 10B. |
| FIG. 10C. | FIG. 10D. |

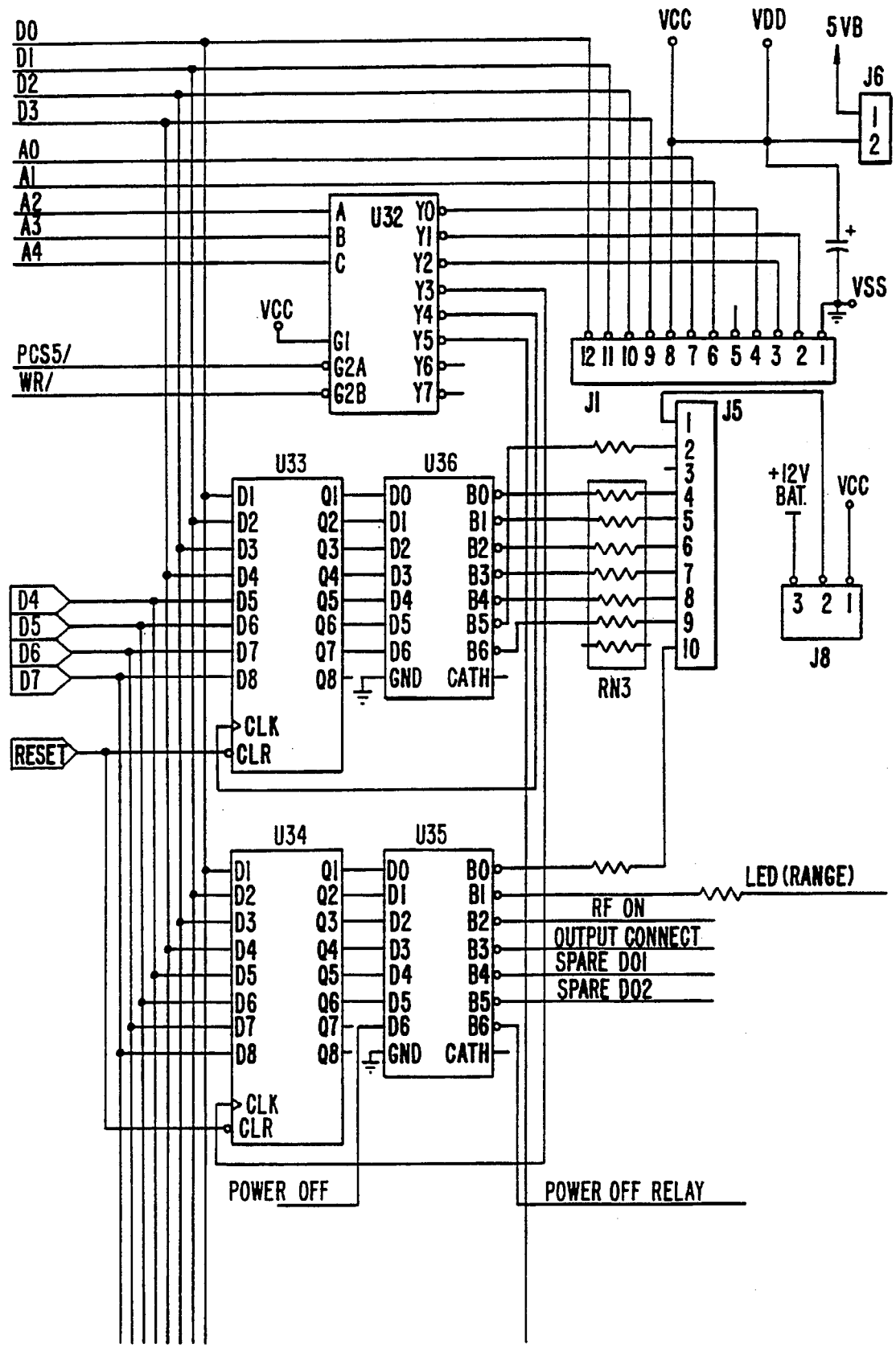
FIG. IIA.

METHOD AND SYSTEM FOR RADIOFREQUENCY ABLATION OF CARDIAC TISSUE

BACKGROUND OF THE INVENTION

1. Field of the Invention

The present invention relates generally to the field of electrophysiology. More particularly, this invention relates to methods and apparatus for treating cardiac arrhythmias.

Symptoms of abnormal heart rhythm are generally referred to as cardiac arrhythmias, with an abnormally slow rhythm being classified as a bradycardia and an abnormally rapid rhythm being referred to a tachycardia. The present invention is concerned with the treatment of tachycardias which are frequently caused by the presence of an "arrhythmogenic site" or "accessory atrioventricular pathway" close to the inner surface of one of the chambers of the heart. The heart includes a number of normal pathways which are responsible for the propagation of signals necessary for the normal electrical function. The presence of arrhythmogenic sites or accessory pathways can bypass or short circuit the normal pathways, potentially resulting in very rapid heart contractions, referred to as tachycardias. Tachycardias may be defined as ventricular tachycardias (VT's) and supraventricular tachycardias (SVT's). VT's originate in the left or right ventricle and are typically caused by arrhythmogenic sites associated with a prior myocardial infarction. SVT's originate in the atria and are typically caused by an accessory pathway.

Treatment of both ventricular and supraventricular tachycardias may be accomplished by a variety of approaches, including drugs, surgery, implantable pacemakers/defibrillators, and catheter ablation. While drugs may be the treatment of choice for many patients, they only mask the symptoms and do not cure the underlying cause. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. The catheter-based treatments rely on the application of various destructive energy sources to the target tissue, including direct current electrical energy, radiofrequency electrical energy, laser energy, and the like.

Of particular interest to the present invention are radiofrequency ablation protocols which have proven to be highly effective in tachycardia treatment while exposing the patient to minimum side effects and risks.

Radiofrequency catheter ablation is generally performed after an initial mapping procedure where the location of the arrhythmogenic sites and accessory pathways are determined. After mapping, a catheter having a suitable electrode is introduced to the appropriate chamber and manipulated so that the electrode lies proximate the accessory pathway. Radiofrequency energy is then applied through the electrode to the cardiac tissue in order to ablate a region of the tissue which forms part of the accessory pathway. By successfully destroying that tissue, the accessory pathway or arrhythmogenic site is destroyed so that the abnormal signalling patterns responsible for the tachycardia will no longer occur.

While very promising, radiofrequency ablation suffers from certain disadvantages. The application of radiofrequency energy to the heart tissue can have complications, particularly if the directed energy has not been properly controlled. Many systems which have been used thus far for radiofrequency ablation have utilized radiofrequency power supplies originally intended for electrosurgery and electrocautery. While such power supplies are workable, they do not provide power control of a type which is best used with cardiac tissue ablation and can subject the patient to spurious ground potentials. Such ground potentials can be a problem when the heart is being treated. Such conventional radiofrequency power supplies are also usually bulky and relatively heavy because of the need to provide power supply transformers.

2. Description of the Background Art

The successful treatment of supraventricular and ventricular tachycardias by radiofrequency catheter ablation of accessory atrioventricular pathways is described in Kuck et al. (1991) Lancet 337:1557–61; Langberg et al. (1991) Am. J. Cardiol. 67:142–47; and Kuck et al. (1991) Circulation 84:2366–2375. Catheters useful for the intracardiac application of radiofrequency energy are described in U.S. Pat. Nos. 4,945,912; 4,940,064; and 4,641,649. A power supply and radiofrequency ablation catheter suitable for intracardiac tissue ablation are available from Dr. Osypka GMBH under the tradenames HAT 200 S and CERABLATE®, respectively. The power supply and catheter together permit ablation to be performed under a digital temperature control mode. The present state of cardiac radiofrequency ablation treatment is summarized in Fackelmann (1991) Science News 140:42–43.

SUMMARY OF THE INVENTION

The present invention is safety feature to prevent injury to a patient due to a malfunctioning temperature sensing device such as a thermocouple.

According to one aspect of the invention, the magnitude of a temperature sensing signal is compared to a reference value indicating the normal body temperature of a patient. Prior to performing ablation the temperature of the catheter should be about equal to the temperature of the patient. Accordingly, if the temperature output signal indicates a temperature that is very different than the temperature of the patient the temperature sensing device is probably malfunctioning. Serious problems could result because the temperature sensing device is used to control the procedure. Thus, the treatment procedure is disabled if the comparison indicates that magnitude of the temperature sensing signal is not almost the same as the magnitude of the reference value.

Other advantages and features of the invention will be apparent to persons skilled in the art in view of the following detailed description and appended drawings.

DESCRIPTION OF SPECIFIC EMBODIMENTS

The method and apparatus of the present invention are intended for delivering radiofrequency energy to a target location within an interior chamber within a patient's heart, usually the right or left ventricle. The target location will be associated with cardiac tachycardia, usually being an accessory pathway or an arrhythmogenic site responsible for the tachycardia, but also including regions on the bundle of HIS which can non-specifically block tachycardia. Accessory pathways or arrhythmogenic sites responsible for the tachycardia can be identified by conventional intracardiac mapping, as is now amply described in the medical and patent literature. See, for example, U.S. Pat. Nos. 4,699,147; 4,628,937; and 4,660,571, the disclosures of which are incorporated herein by reference. See also copending application Ser. No. 07/866,763 the disclosure of which is incorporated herein by reference.

Radiofrequency ablation involves the application of radiofrequency energy, typically at a frequency in the range from about 250 to 1000 kHz, usually in the range from about 400 to 500 kHz, at a power level sufficient to raise the target tissue to a sufficiently high temperature for a time sufficient to induce tissue necrosis. Typically, the tissue temperature will be above about 45° C., usually being above about 60° C., but usually not exceeding about 105° C., and preferably being maintained below about 95° C. For such temperatures, the radiofrequency energy will typically be applied for time periods in the range from about 30 to 60 seconds, but time periods as short as 10 seconds and as along as 90 seconds also find use.

In order to deliver the radiofrequency energy to the desired target location within the heart, an intravascular catheter having a suitable electrode near its distal end will be percutaneously introduced, typically through the femoral vein or artery in the patient's groin. The distal tip of the catheter can then be manipulated by conventional means, typically through a previously introduced guiding catheter, until it reaches the interior of the heart. The electrode tip of the catheter will then be further manipulated so that it contacts the desired region within the interior of the heart chamber, typically the location of an accessory pathway, a location on the bundle of HIS, an arrhythmogenic site in the ventricular wall, or the like. Radiofrequency power will then be applied to the target location according to the method of the present invention, as described in more detail hereinafter. Preferably, the radiofrequency power will be applied using a radiofrequency generator and system of the present invention, also as described in more detail hereinafter.

Figure 1:
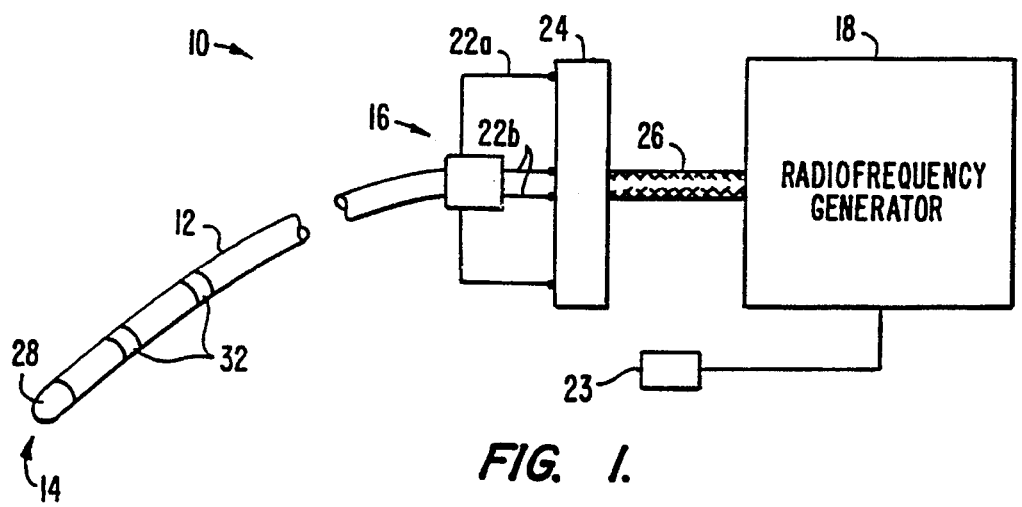
FIG. 1 is a schematic illustration of a system for radiofrequency ablation of cardiac tissue constructed in accordance with the principles of the present invention, comprising a catheter connected to a radiofrequency generator.

Referring now to FIG. 1, an exemplary radiofrequency ablation system 10 constructed in accordance with the principles of the present invention includes a catheter 12 having a distal end 14, a proximal end 16, and a radiofrequency generator 18 connected to the catheter as described below. The proximal end 16 of the catheter 12 includes a proximal housing 20 having a plurality of connecting wires 22 that will normally terminate in a connector 24. The radiofrequency generator 18 is connected to the connector 24 through a cable 26. In this way, all active electrical components (as described hereinafter) of the catheter 12 may be removably connected to the radiofrequency generator 18 simply by plugging the catheter connector 24 into the cable 26.

Figure 2:
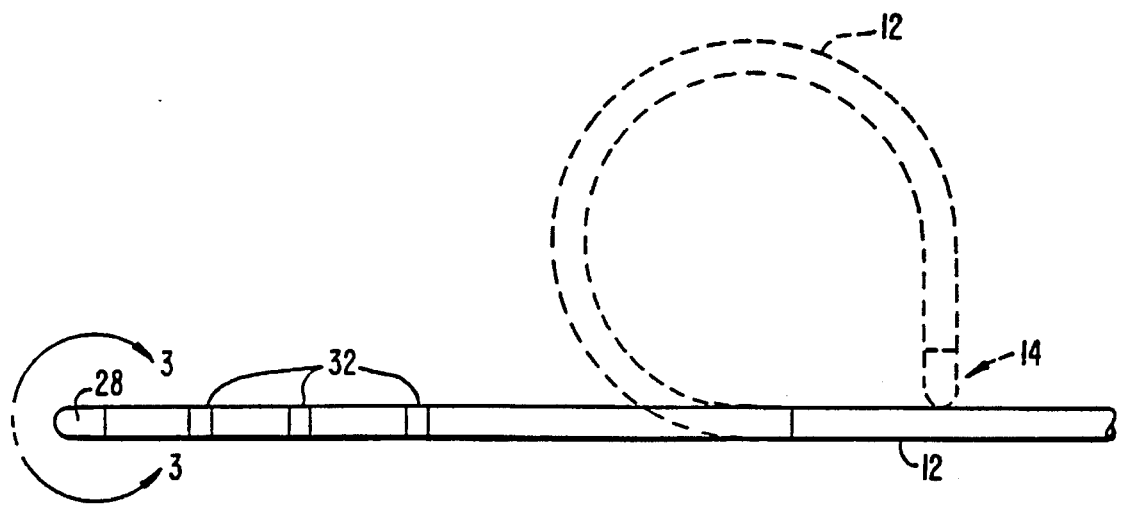
FIG. 2 is an enlarged view of the catheter of FIG. 1, with a curved tip shown in broken line.
Figure 3:
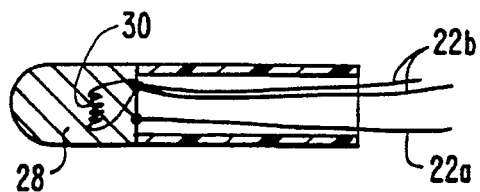
FIG. 3 is a detailed view of the catheter of FIGS. 1 and 2, shown in section.

Referring now to FIGS. 1–3, the catheter 12 includes an electrode 28 near its distal end, usually being at the distal tip, which is connected to a wire 22a which provide a monopolar power connection to the electrode 28 for applying radiofrequency energy from the generator 18, as will be described in greater detail hereinafter. An indifferent electrode 23 is separately connected to the generator 18 and permits attachment to the patient's skin surface to complete the circuit necessary for the application of RF energy as described below. A pair of wires 22b is connected to a temperature sensor 30 located on or in the electrode 28. Typically, the temperature sensor 30 will be a thermocouple consisting of a pair of dissimilar metals, usually copper and constantan which form a T-type thermocouple. The thermocouple wires 22b will also be connected to the radiofrequency generator 18 through the connector 24 and cable 26 so that they will be connected and disconnected as the catheter 12 is plugged and unplugged. The wires 22b may be utilized to verify the electrical continuity of the thermocouple.

The catheter 12 may optionally include additional electrodes 32 axially spaced apart over the distal end 14. Electrodes 32 will usually be provided to permit ECG monitoring prior to, during, and/or after the radiofrequency ablation treatment. Additional connectors (not illustrated) will be provided so that the electrodes 32 may be connected to external monitoring equipment (not illustrated) through the connector 24 and cable 26. Usually, the radiofrequency generator 18 will include provisions for connecting such monitoring equipment to the catheter 12. Optionally, the electrodes 32 may be used to perform initial mapping to locate the accessory pathways in a generally conventional manner. These aspects of the catheter, however, do not relate directly to the present invention and will therefore not be described in detail.

Catheter 12 preferably includes a deflectable distal tip which permits deflection, as illustrated in broken line in FIG. 2. A variety of control mechanisms (not illustrated) may be provided to effect such tip deflection as described generally in the medical and patent literature. Preferred tip deflection mechanisms are described in copending application Ser. Nos. 07/866,383 and 07/867,241, the disclosures of which are incorporated herein by reference.

Figure 4:
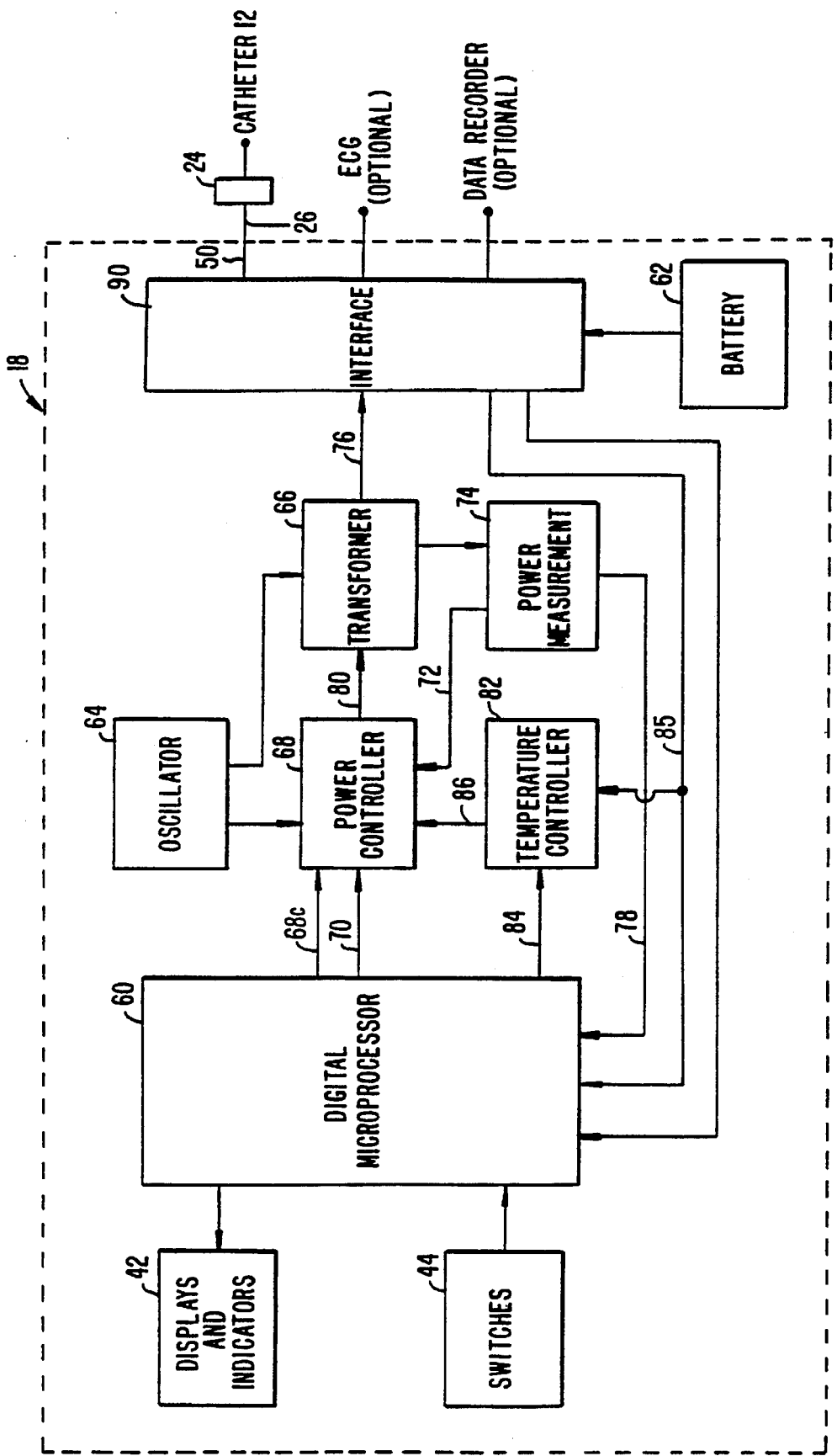
FIG. 4 is a block diagram of the circuitry of a radiofrequency generator constructed in accordance with the principles of the present invention.
Figure 5:
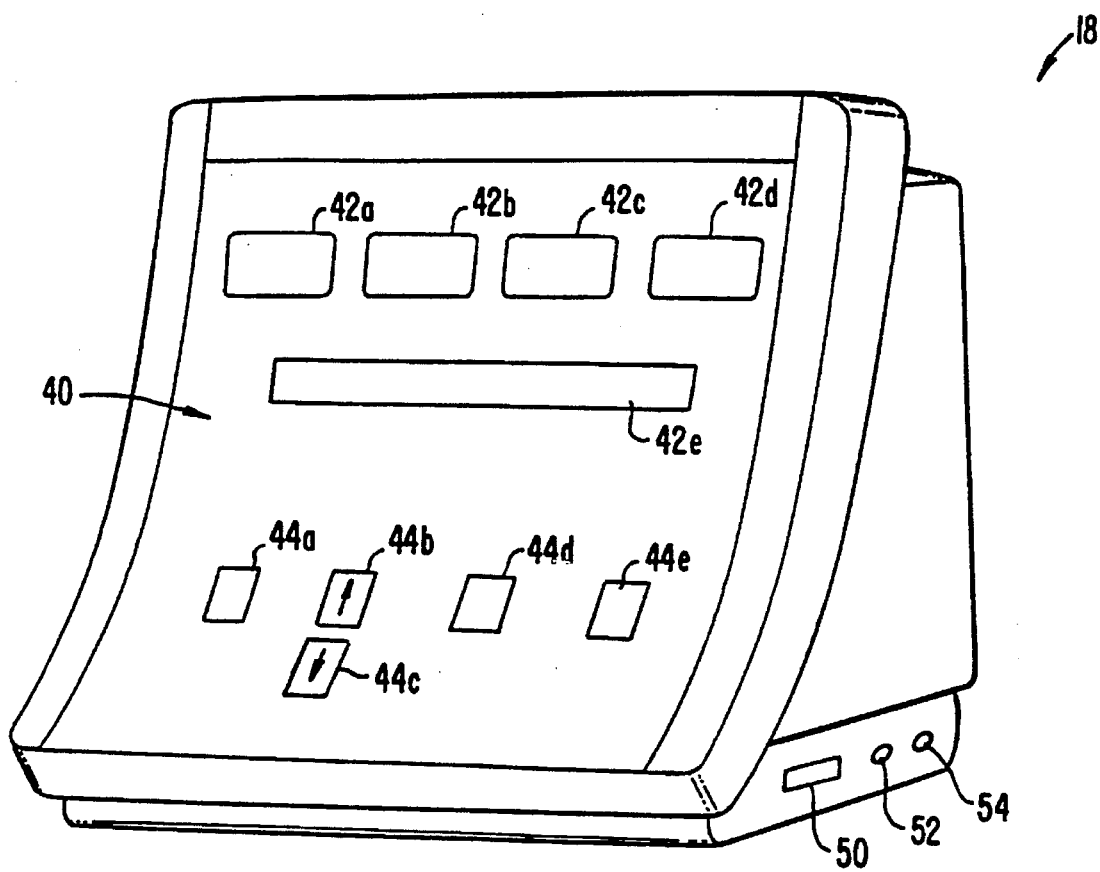
FIG. 5 illustrates the exterior of a power supply system constructed in accordance with the principles of the present invention.

Referring now to FIGS. 4 and 5, the radiofrequency generator 18 of the radiofrequency ablation system 10 will be described in more detail. Radiofrequency generator 18 includes a user interface panel 40 having a plurality of displays and indicators 42, switches 44 and legends (not illustrated), to permit the operator to monitor and control delivery of power to the catheter 12, as will be described in greater detail hereinafter. In particular, the indicators 42 and switches 44 permit monitoring and control of the amount of radiofrequency power delivered to the catheter 12 by radiofrequency generator 18. The panel 40 includes a first display 42a which provides a continuous digital readout of the actual radiofrequency power being delivered (usually calibrated in Watts). A second display 42b shows the actual electrode temperature measured by the thermocouple 30 (FIG. 3). A third display 42c shows the calculated impedance (based on measured current and voltage) between the catheter ablation electrode 28 and an indifferent electrode during the delivery of radiofrequency energy. The indifferent electrode is attached to the patient and provides a return path to complete the circuit to the tip electrode 28. A sudden rise in impedance indicates that coagulum has formed on the tip, which should be removed. A fourth display 42d provides an indication of the time that radiofrequency power has been delivered during an ablation procedure.

The panel 40 further include an alphanumeric display 42e which presents additional information to the user, depending on the operational mode selected as described below. Such information includes the set point for either temperature (in °C.) or power (in Watts), depending on the control mode. The display 42e can further set forth the total number of cycles, i.e. the number of times that power supply to the ablation electrode 28 has been initiated. The display 42e can further indicate total treatment time, i.e. the total elapsed time that the radiofrequency power has been delivered from the time power to the generator 18 was turned on. Finally, the legend 42e will indicate the available set point range for power, temperature, or time, depending on the variable which is being set within the system (when a set point is changed).

The alphanumeric 42e can further provide user warnings, including excessively high temperature, unacceptable catheter (when an open circuit in the catheter is detected during a radiofrequency generator verification check, as described below), excessively high impedance, low impedance, and excessively high power. Finally, a legend (not illustrated) will indicate when the battery charge has become low, typically when it reaches 25% of capacity. Conveniently, a tone warning signal will be provided whenever any warning is being displayed.

A switch 44a is provided in order to select the control mode, i.e., either power or temperature. A particular variable (temperature or power) will be adjusted by raising or lowering the set point using the appropriate up or down switch 44b or 44c. The user presses and holds switch 44d and increases the time set point by pressing switch 44b or decreases the time set point by pressing switch 44c. After initiation, the power will be delivered for the total time thus set. The value of the particular variable set point (and allowable range) is displayed on alphanumeric display 42e as the set point is being adjusted.

Switch 44e controls the delivery of RF power. When the RF power generator 18 is first turned on, a legend OFF (not illustrated) is lit. Switch 44e must be pressed to put the unit in standby which also activates an optional foot pedal (not illustrated). Once in standby mode, pressing switch 44e causes RF power to be delivered until either the switch 44e is again pressed or the time set-point is reached, at which time the unit returns to standby. If a warning condition occurs (i.e., high power or high impedance), the unit goes to OFF mode and the optional foot pedal is deactivated.

A main off and on switch is provided on the top of the radiofrequency generator 18. A catheter connector 50, an indifferent electrode connector 52, and a foot pedal connector 54 are provided on the right side of the radiofrequency generator 18. The catheter connector 50 permits plugging in of the catheter connector 24 to cable 26 to provide the necessary connections between the electrical components of the catheter and the generator 18. The foot pedal connector permits connection of a pneumatic foot pedal which allows the treating physician to control the application of radiofrequency power by depressing and holding the foot pedal.

Additional connections on the radiofrequency generator 18 will usually include an ECG connector, an analog output connector which permits output to a multichannel chart recorder for recording radiofrequency power, impedance between the ablation electrode and indifferent electrode, and ablation electrode temperature. An additional connector will usually be provided to permit connection of the internal microprocessor to an external computer to monitor and temporarily override programming in the PROMS. The connector will usually be a conventional RS-232 connector which is compatible with standard IBM-type personal computers. A switch may also be provided to permit the operator to set the volume level of the tone during the RF ablation. Finally, a TUV connector will be provided for connection to an external ground.

Referring now to FIG. 4 in particular, the front panel displays and indicators 42 and switches 44 will be connected to a digital microprocessor 60, such as an INTEL 80C 186, which permits interface between the user and the remainder of the electrical components of the system. In particular, the microprocessor 60 provides for continuous monitoring of power, current, voltage, temperature, impedance, and battery level. As necessary, the microprocessor will provide this information to the appropriate display and/or indicator 42 on the front panel 40. Additionally, the microprocessor 60 permits the user to select the control mode (either constant temperature or constant power) and to input the power set point, temperature set point, and timer set point to the system.

The primary source of power for the radiofrequency generator 18 is a battery 62, typically a 12 V battery rated at 7.2 ampere-hours. A back-up battery (usually a lithium cell; not illustrated) will be provided to provide sufficient power to the microprocessor 60 to maintain desired memory functions when the main power from battery 62 is shut off.

A crystal-locked radiofrequency oscillator 64 generates the switching pulses which drive both the power transformer 66 and the power controller 68. Power controller 68 is an analog controller which operates by pulse-width modulation by comparing a power set point signal 70 (from microprocessor 60) with an actual power signal generated by a power measurement circuit, typically a torroidal transformer coupled to the power output 76 from the transformer 66. The power measurement component 74 multiplies the output current and voltage and provides the resulting actual power signal to both the power controller through line 72 and the microprocessor through line 78. Separate analog comparator circuits (not illustrated) are provided for monitoring the output of the power measurement component 74 in order to shut-off current to the output transformer if the power exceeds a limit, typically 55 watts.

Power transformer 66 includes a center tap which receives the output 80 of the analog power controller 68. Secondary winding provides for continuous monitoring of the applied voltage in order to permit the power calculations by power measurement circuit 74.

Figure 12A:
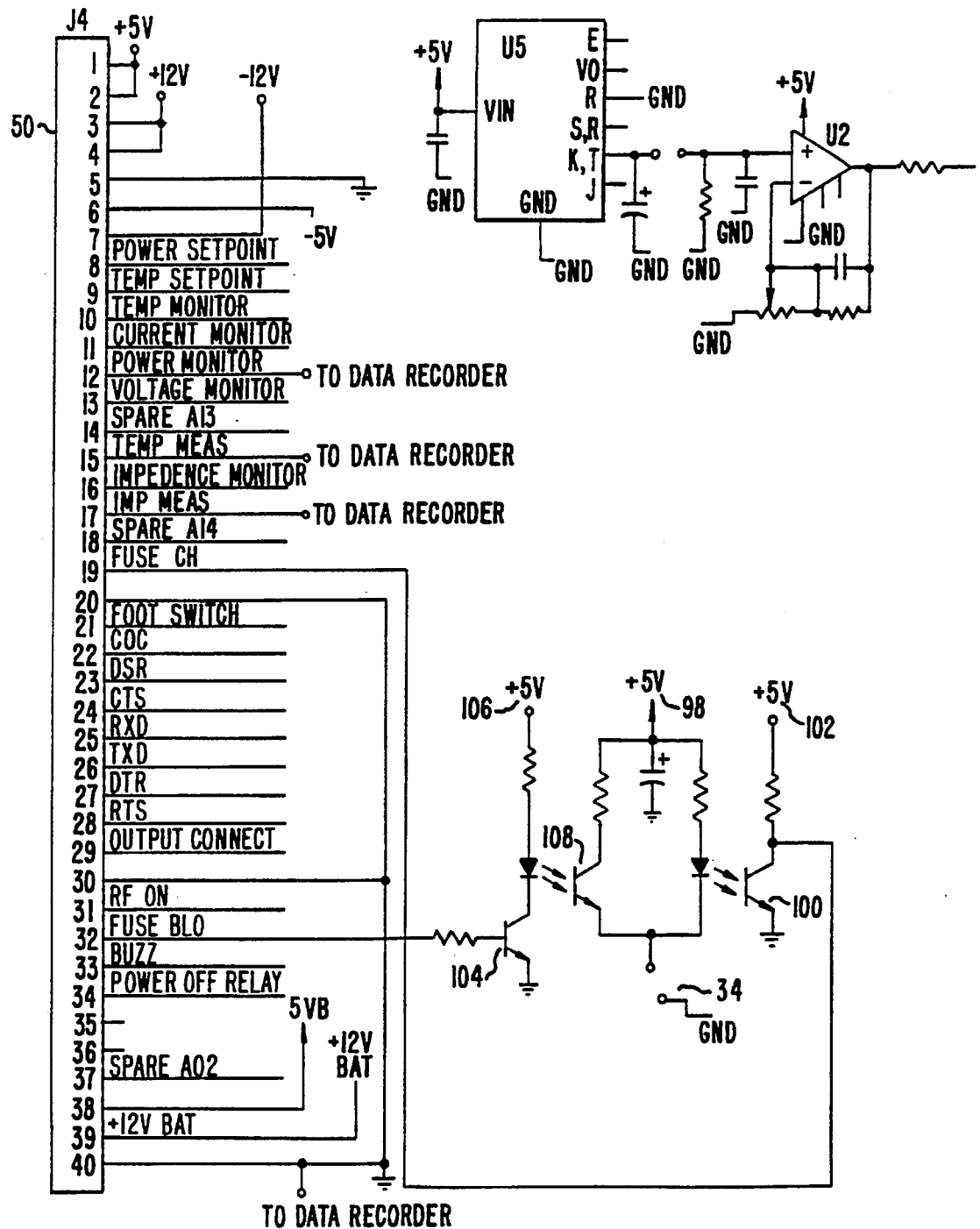
Figures 12, 12B:
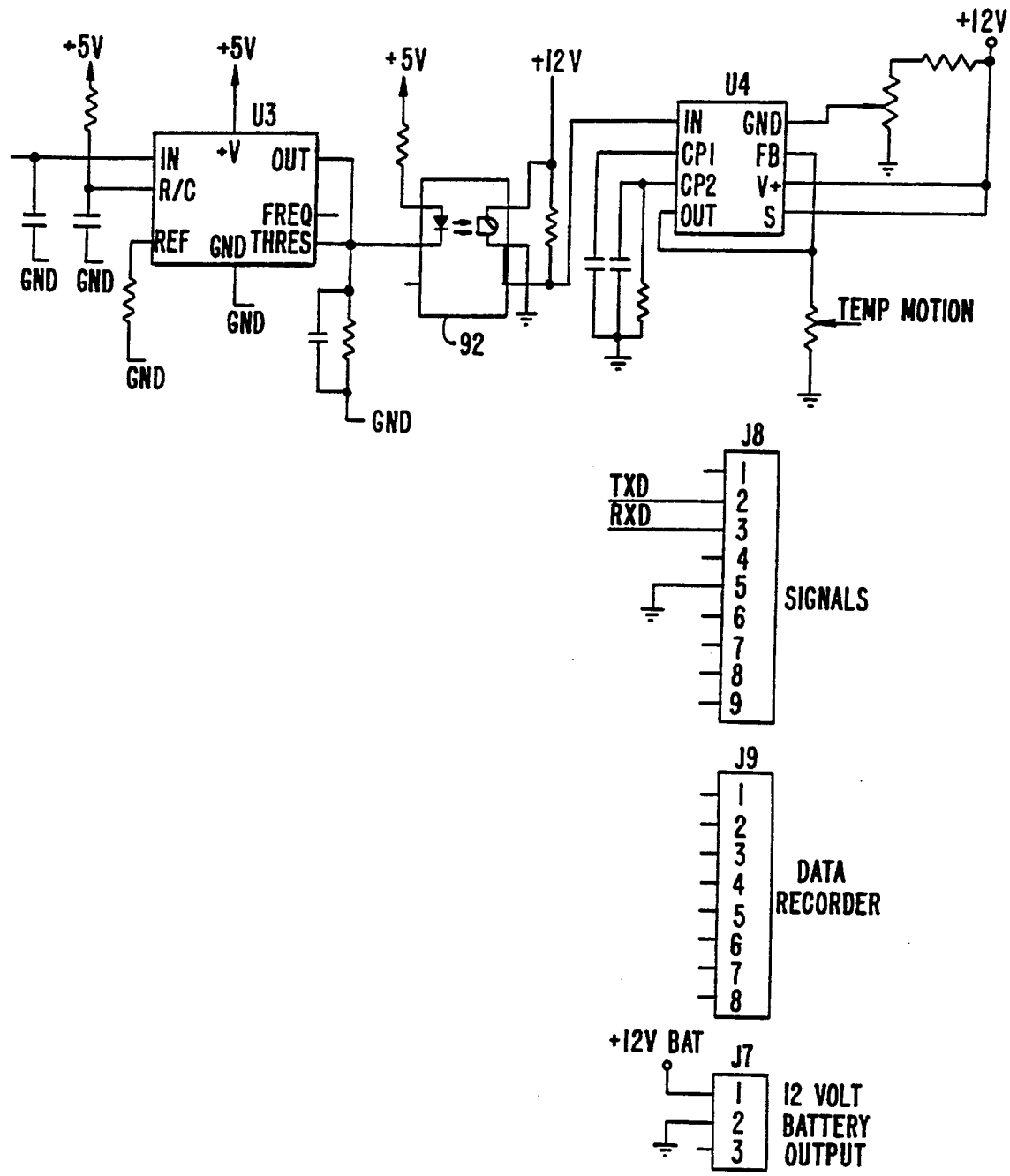
Figure 12C:
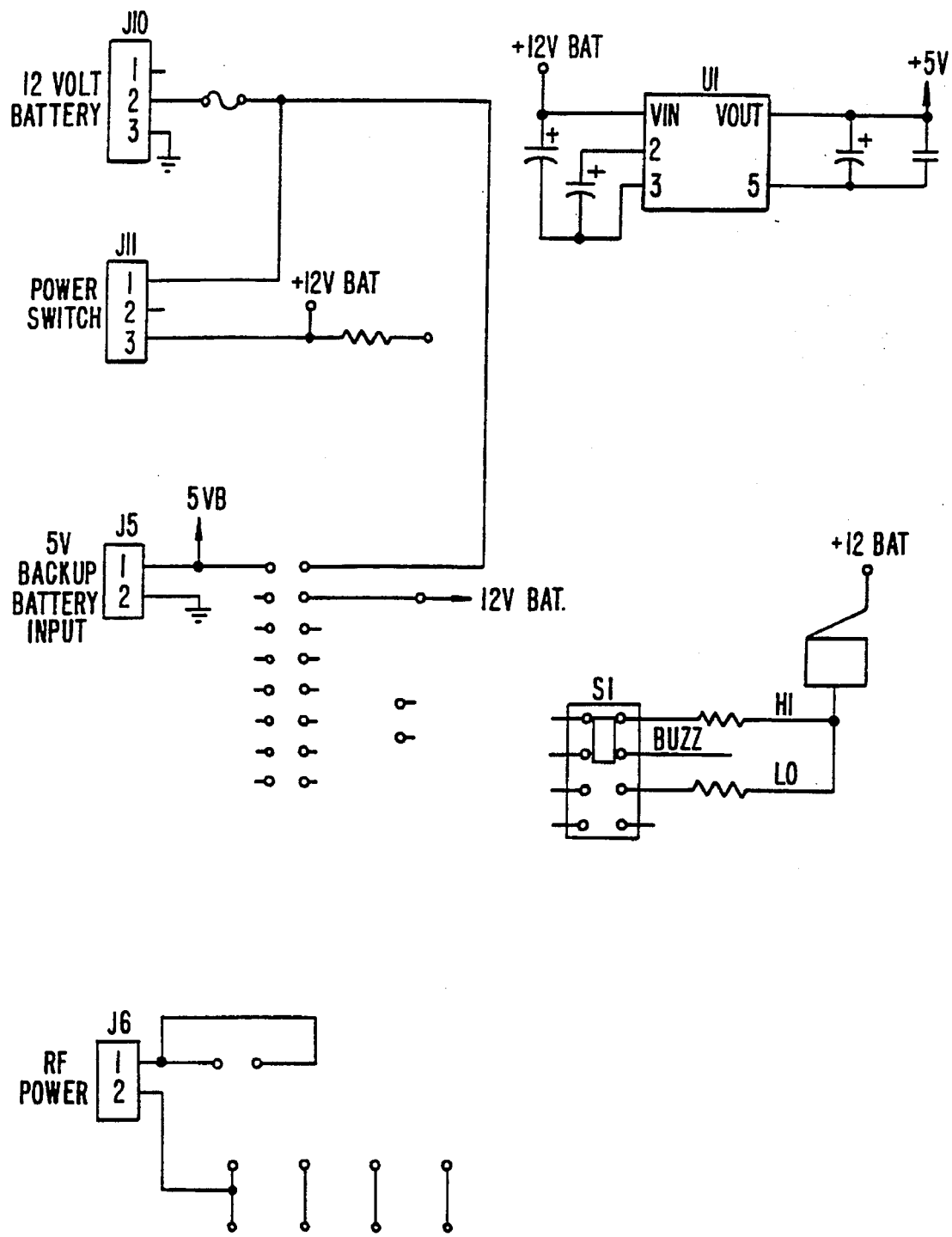

In a preferred aspect of the present invention, an analog temperature controller 82 is provided to permit operation in a temperature control mode. A temperature set point is delivered to the temperature controller 82 from the microprocessor 60 through line 84 and the thermocouple output signal is delivered to the temperature controller 82 and to microprocessor 60 through line 85. Analog controller 82 operates on a proportional control mode, producing a power set point 86 which is fed to the power controller 68. Power set point 86 replaces the set point 70 when the system is in temperature control mode operation. The analog power controller 68 thus acts as a cascade control loop in a two-stage temperature control protocol. It has been found that such two-stage analog control permits precise and very fast control of power to maintain the desired temperature set point at the ablation electrode 28. In particular, the control scheme permits very rapid temperature rise to the desired temperature set point with minimum overshoot and very close temperature maintenance throughout the duration of the radiofrequency ablation cycle. The temperature will usually be maintained within ±5° C. of the set point, more usually being maintained to within ±2° C. of the set point. Separate analog comparator circuits 90, illustrated in FIG. 12, are provided for monitoring the temperature of the thermocouple 30 in order to shut-off current to the output transformer if the temperature exceeds a limit, typically about 100° C.

All external connections to the radiofrequency generator 18 will be made through an interface board 90. The interface board 90 permits connection of the main battery 62 and back-up battery (not illustrated), as well as the catheter connector 50, the ECG connector, the data recorder connector, and the like. Connection of the thermocouple will be optically isolated from the internal components of the radiofrequency generator 18 by optoisolator 92, shown in FIG. 12. The data recorder outputs on the RF generator 18–94 may be optically isolated if necessary to reduce signal noise. Such isolation provides both patient safety as well as isolation of the internal components of the generator 18 from the radiofrequency power which is being delivered to the patient.

The detailed circuitry necessary to construct the radiofrequency generator 18 is set forth in detail in the appendix attached to this application. The appendix includes six circuit diagrams, where each circuit diagram is labeled to indicate the components which are included on that diagram.

Figure 6A:
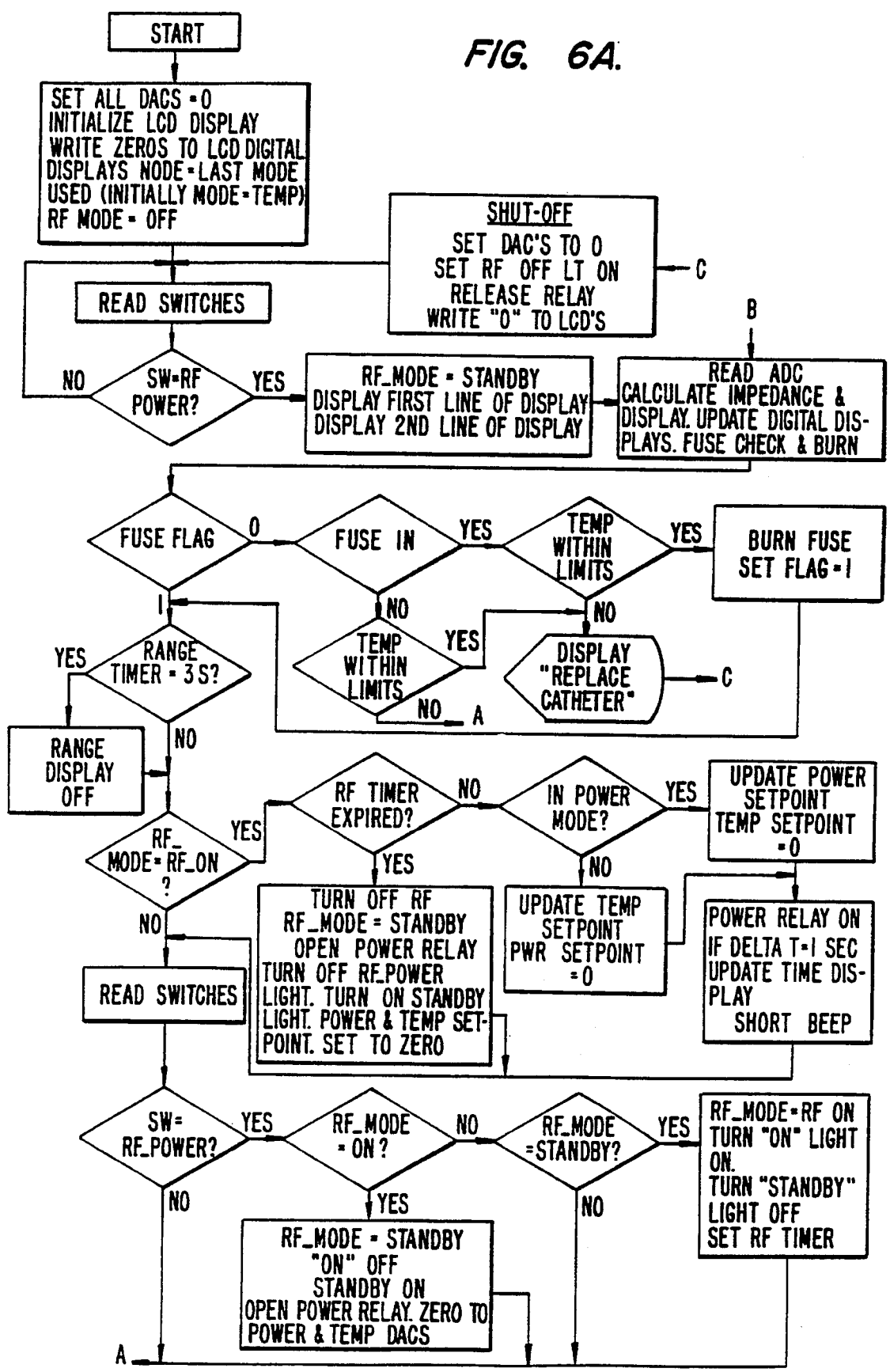
FIGS. 6A and 6B illustrate a flow chart of the operating program of the microprocessor-controlled power system of the present invention.
Figure 6B:
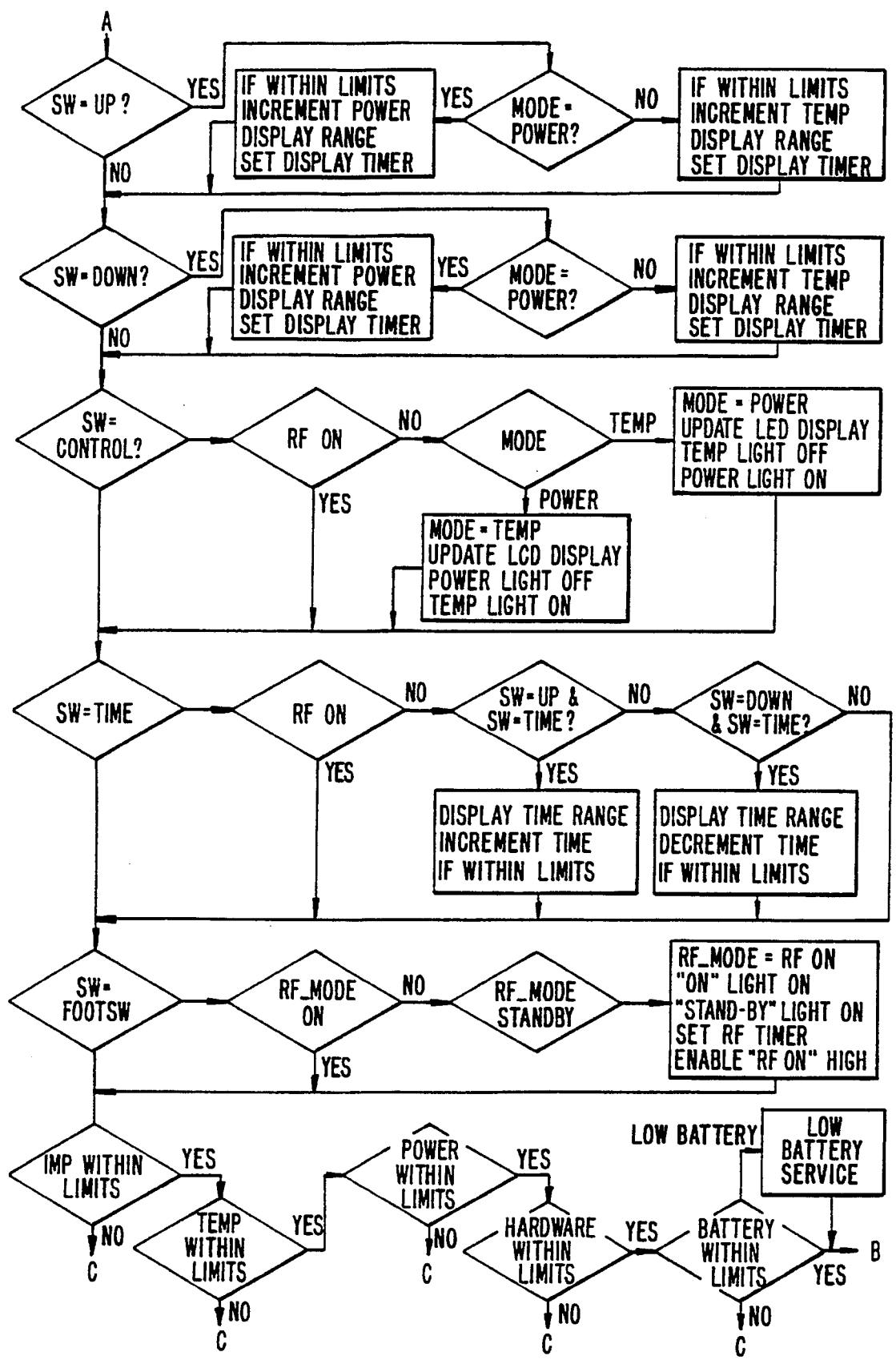

Operation of the microprocessor is schematically illustrated in the flow sheet included in FIGS. 6A and B.

The relationship of the microprocessor 60 to other hardware elements of the RF ATAKR system are shown in FIG. 4. The variable inputs to and outputs from the microprocessor 60 are identified as follows:

| MICROPROCESSOR | |
|---|---|
| From catheter 12: | To catheter 12: |
| Tip electrode temperature<br>Impedance (tip electrode to<br>indifferent electrode) | Power to tip |
| From power controller 68: | To power controller 68: |
| Power level<br>Voltage<br>Current | Start/stop RF power 68c |
| From Panel face 40: | To panel face 40: |
| Control mode<br>Temperature set point<br>Power set point<br>Timer set point<br>RF Power delivery | System status (on, off, standby)<br>Audible alarm<br>Visual alarm<br>Displays (power, temp., impedance,<br>etc.) |

The microprocessor 60 performs the system control function by reading the user, catheter, and generator input values and providing corresponding power on/off commands to the RF power controller 68 and system status and alarm information to the user. The input values for temperature, current, and voltage originate as analog signals and are converted to digital (via digital/analog converters (DAC's)) for the microprocessor. Impedance and power are calculated from current and voltage. Timing is maintained by onboard clock.

Default values of the system are maintained in two ways. Preset default settings are in effect upon initial use and if the backup battery fails. These present default settings are as follows:

| Setting | Default Condition |
|---|---|
| Control Mode | Temperature |
| Temperature set-point | 70° C. |
| Power set-point | 20 Watts |
| Time set-point | 30 seconds |

If the user changes these settings, the last settings entered become the default settings on system power-up providing the backup battery does not fail.

Specific safety features incorporated in the programming of the microprocessor 60 include the following.

In both temperature and power control mode, RF power is applied to the catheter only during the selected cycle time and only when the impedance is within a preset range (typically 25 to 250 ohms). Additionally, power must be below a preset maximum (typically 55 watts maximum), and the temperature must be below a preset maximum (typically to 105° C. when operating in temperature control mode). Also, the catheter must not have been previously used as described earlier.

Figure 7A:
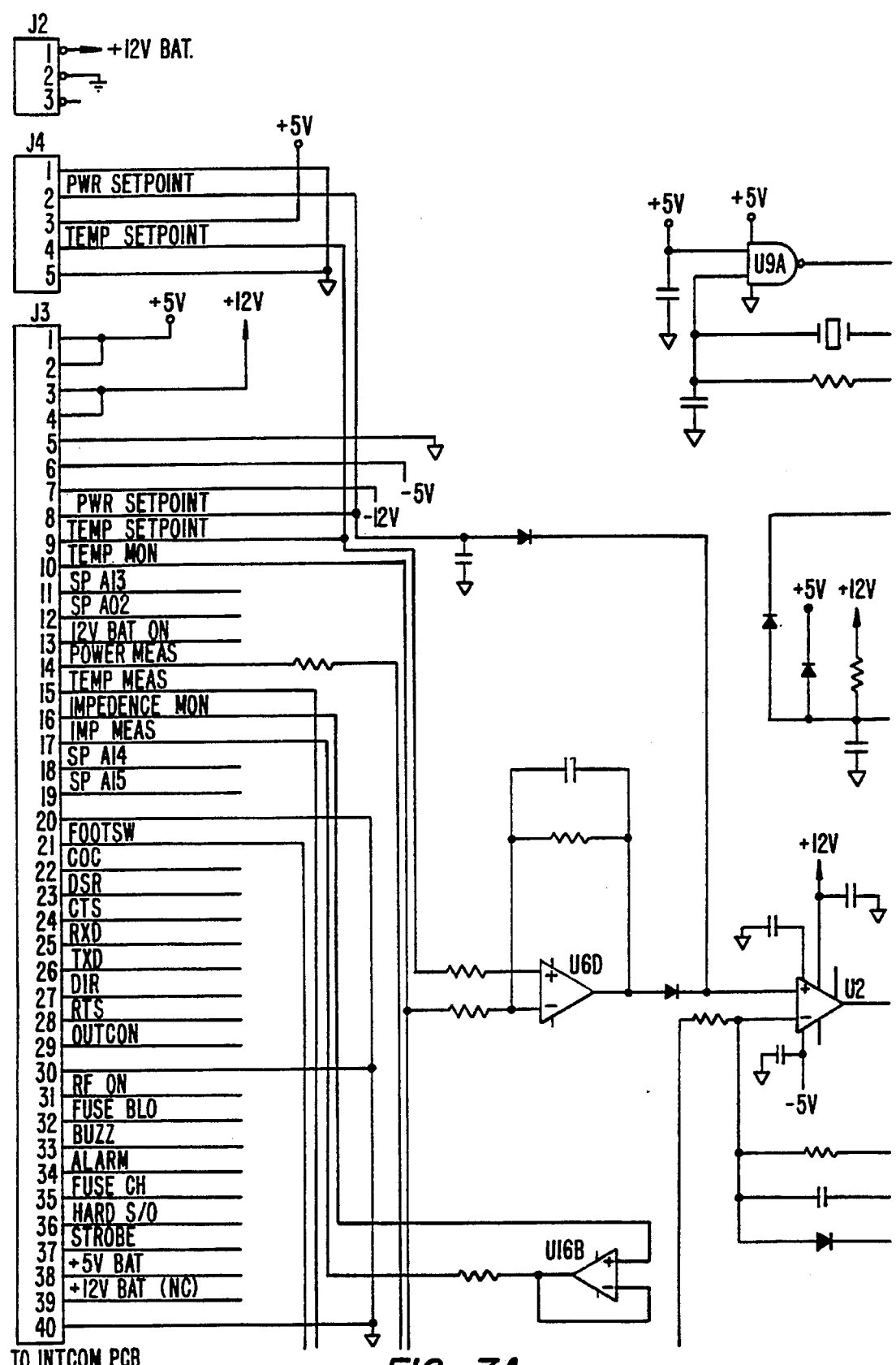
FIGS. 7–12C are schematic diagrams illustrating the circuitry of the radiofrequency generator of FIG. 4.
Figure 7B:
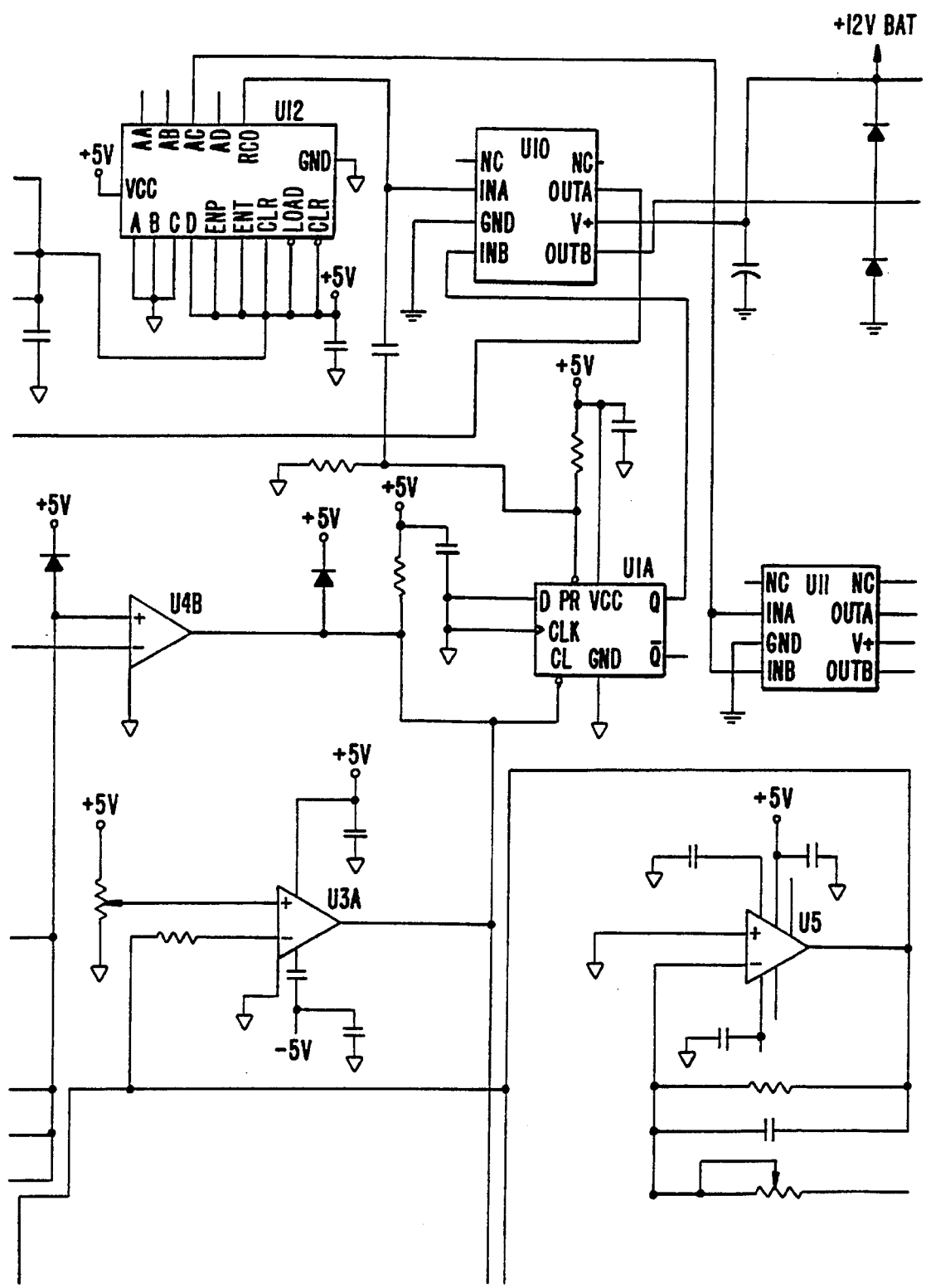
Figure 7C:
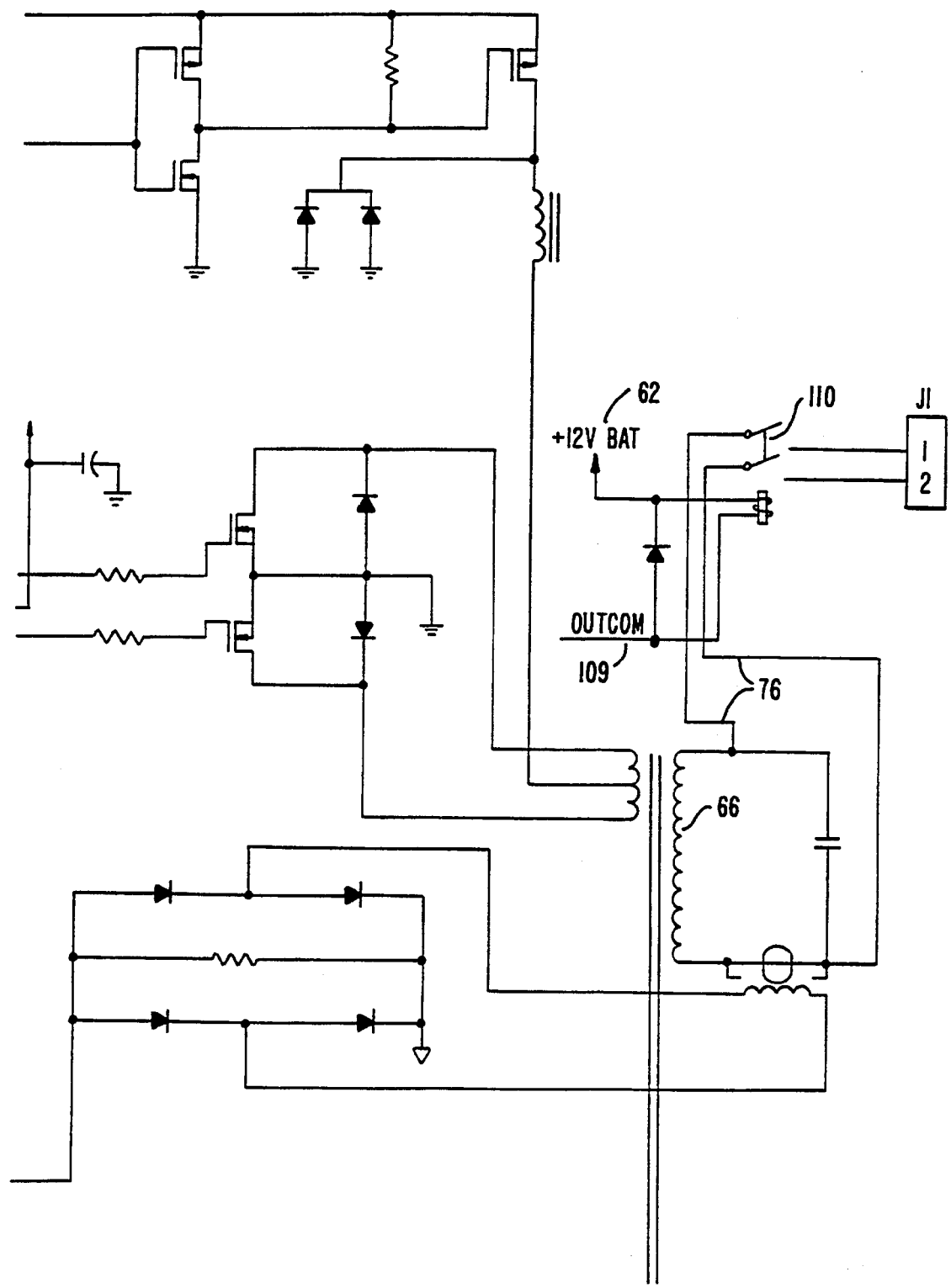
Figure 7D:
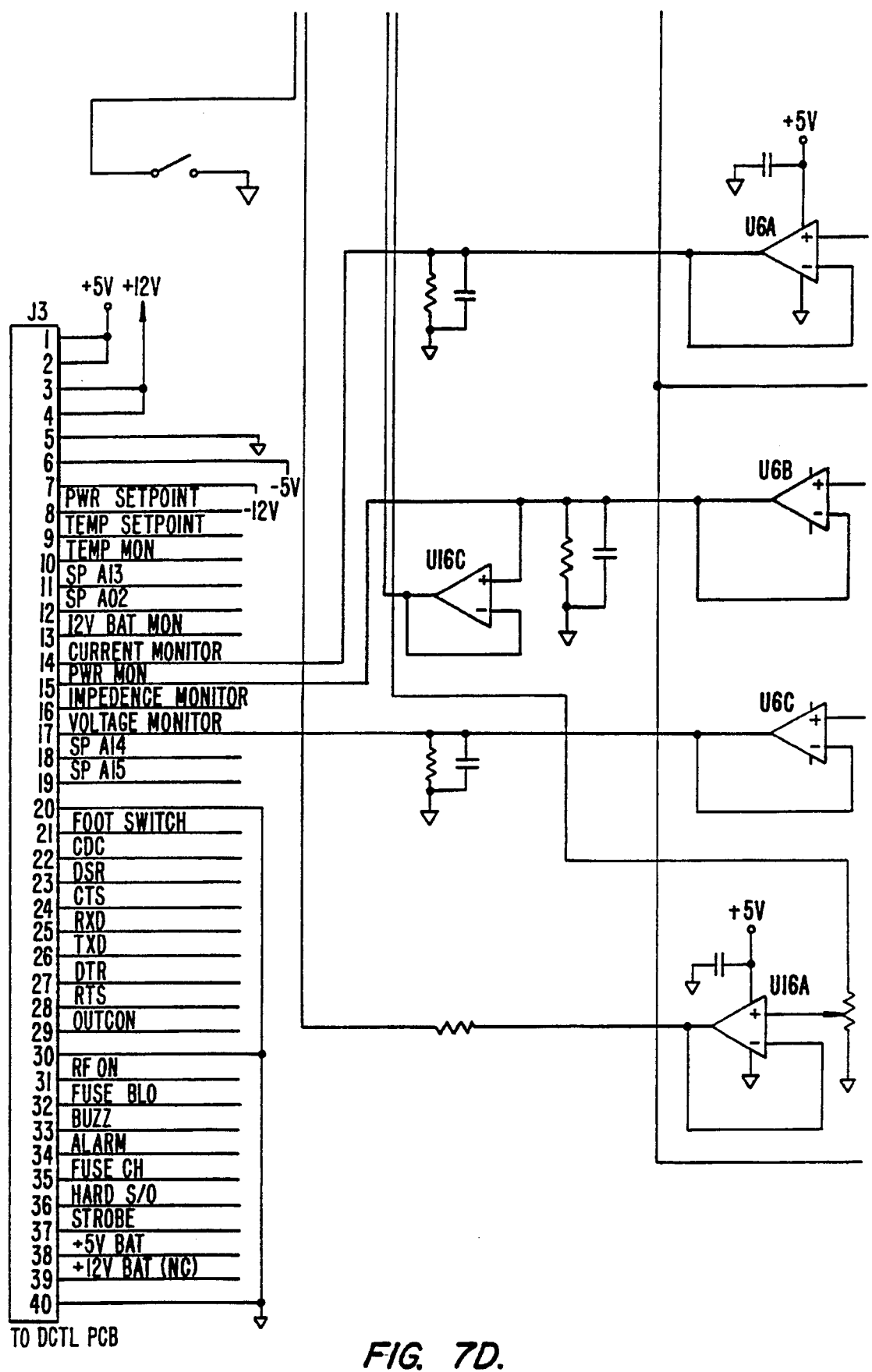
Figure 7E:
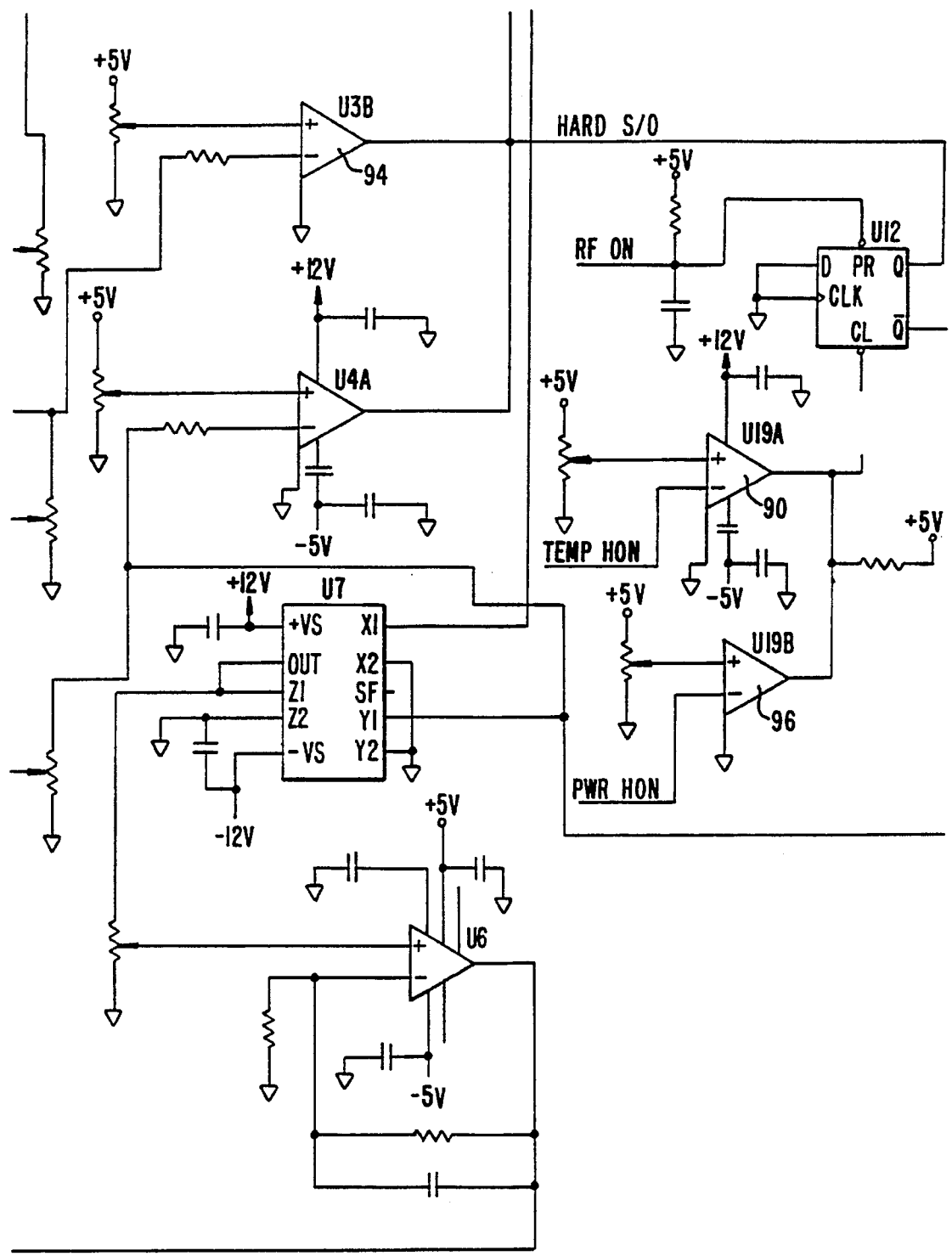
Figures 7, 7F:
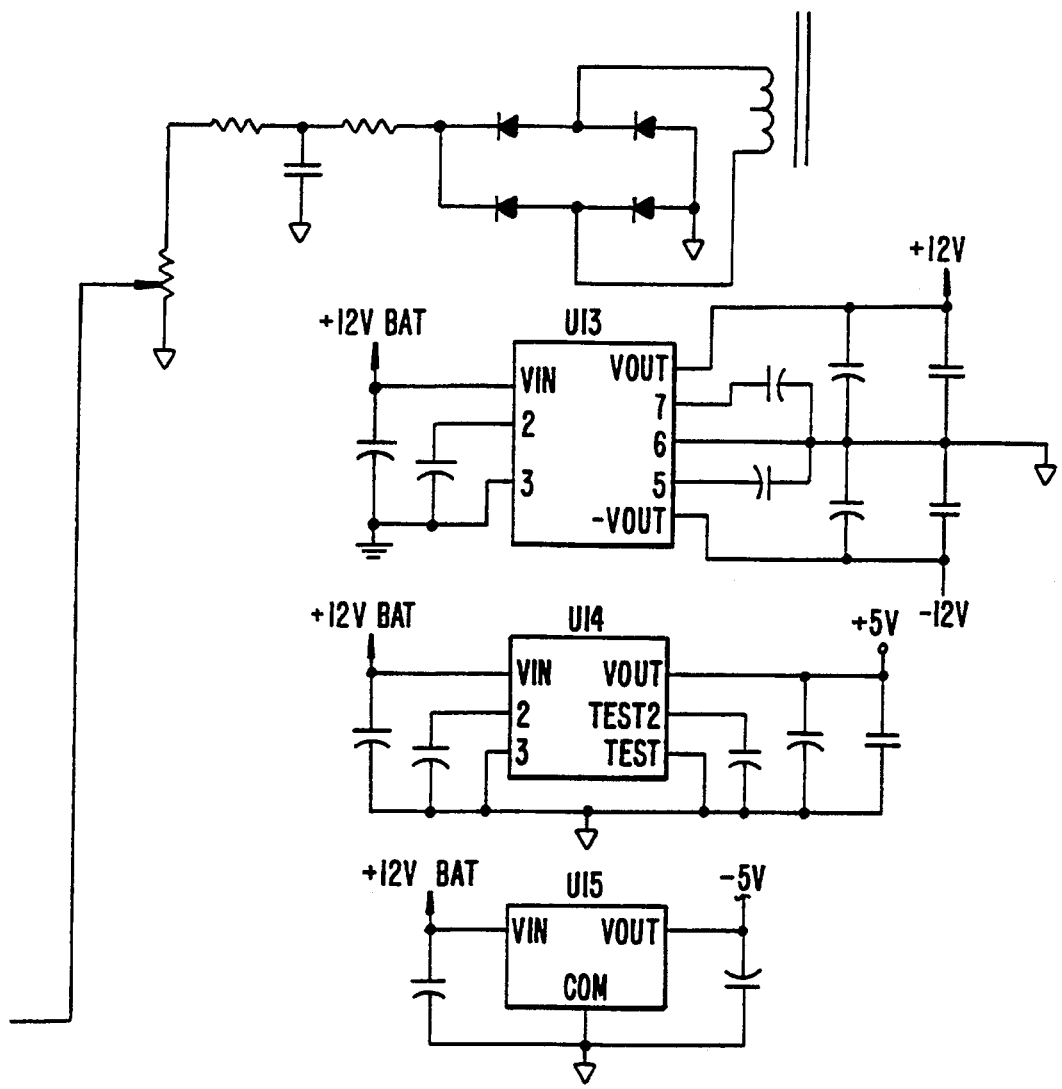
Figures 8, 8A:
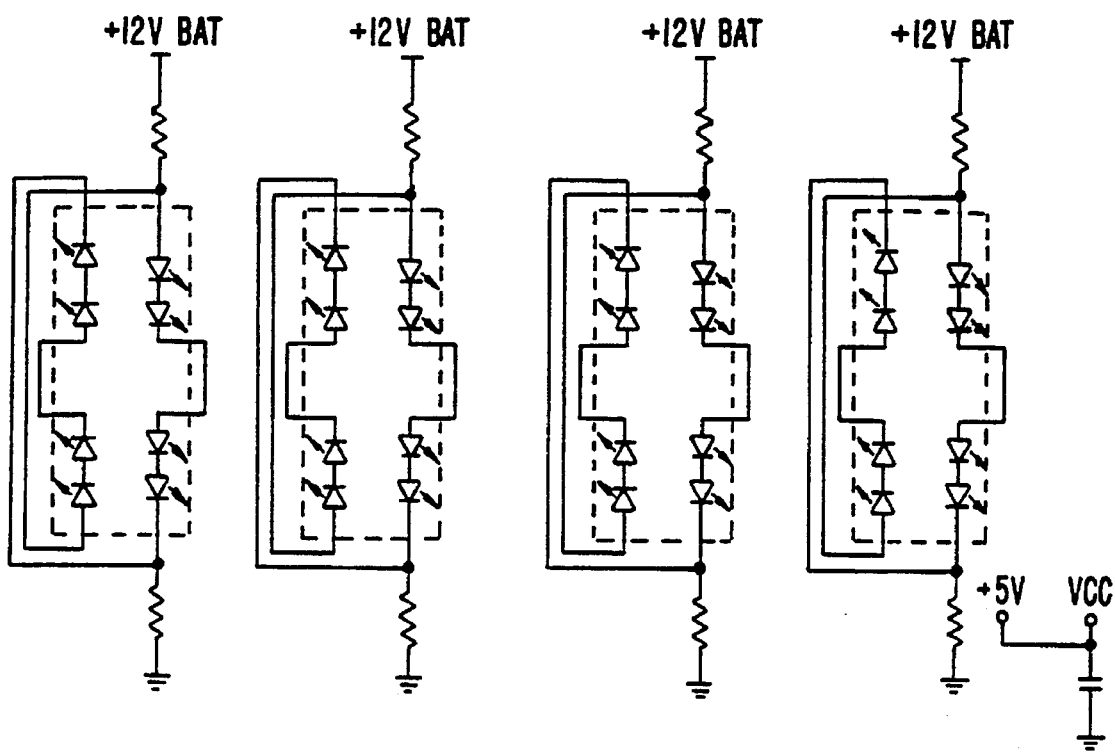
Figure 8B:
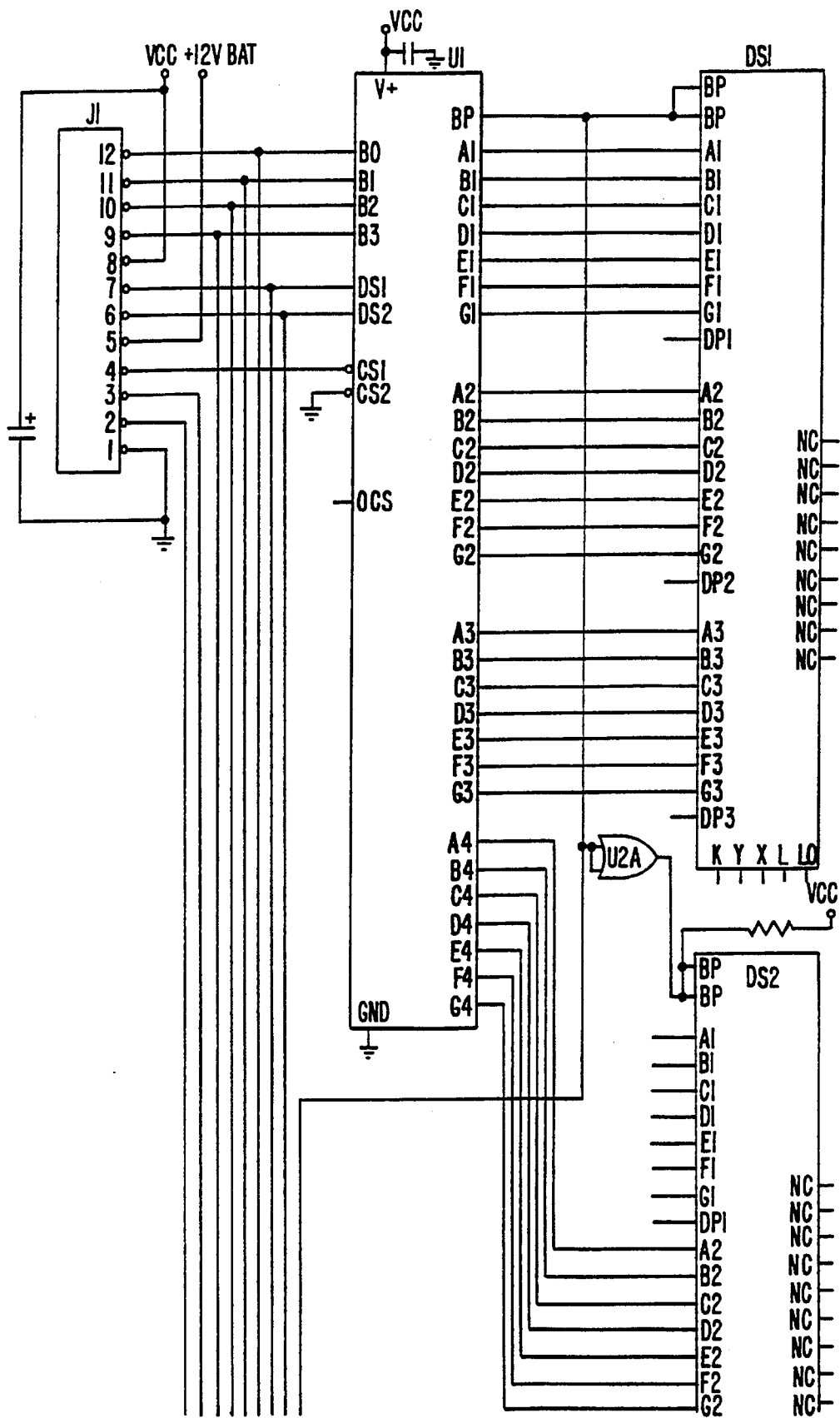
Figure 8C:
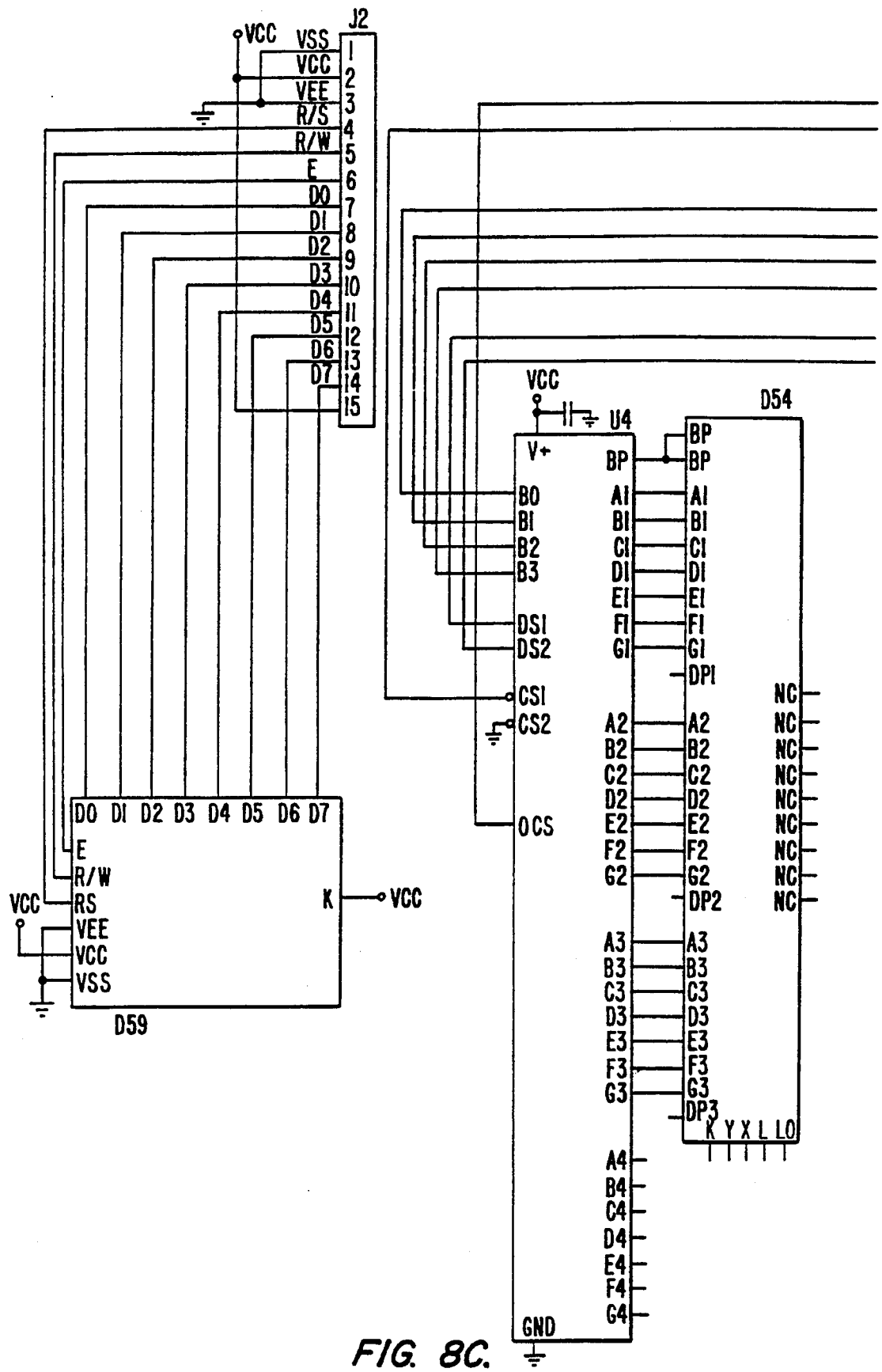
Figure 8D:
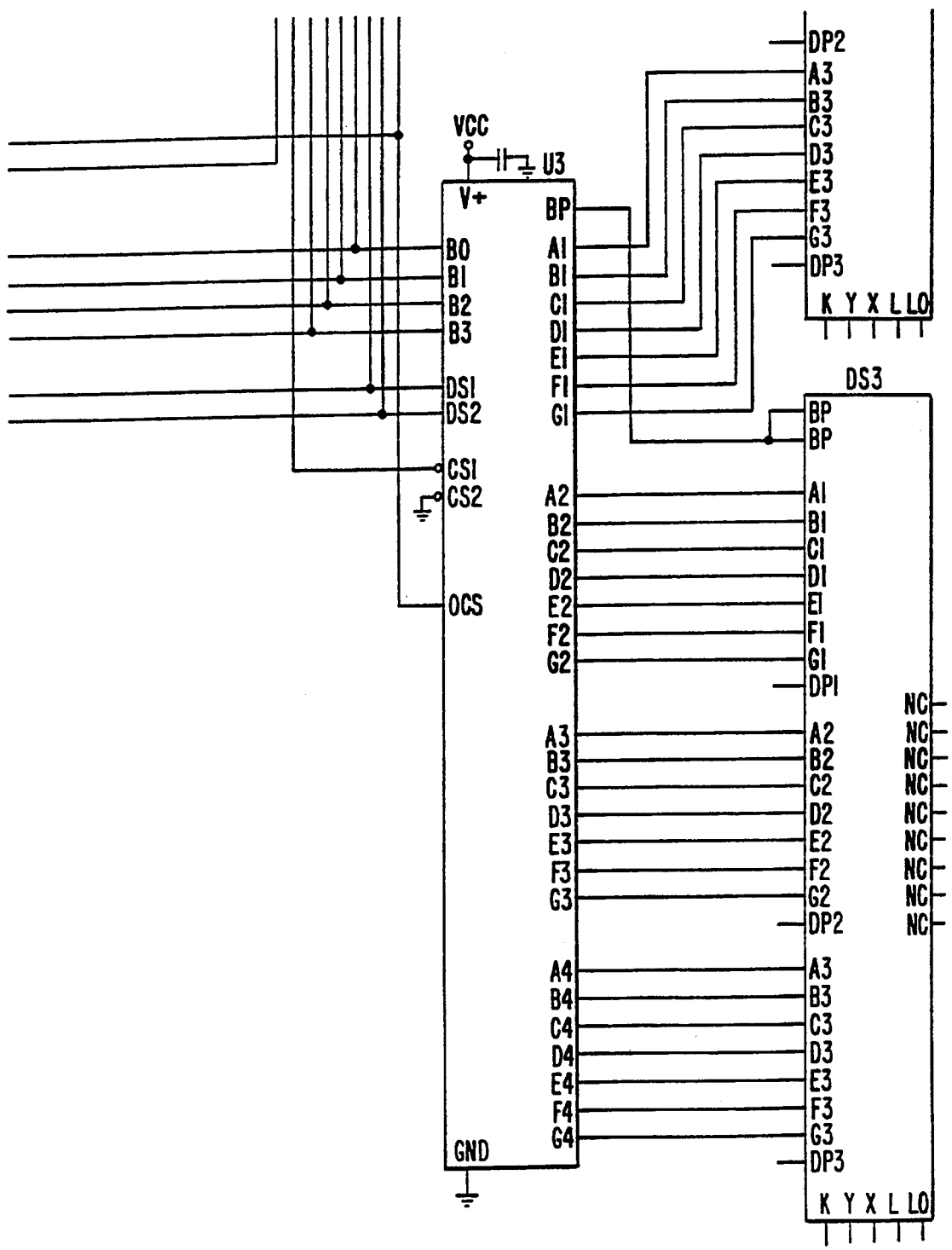
Figure 9A:
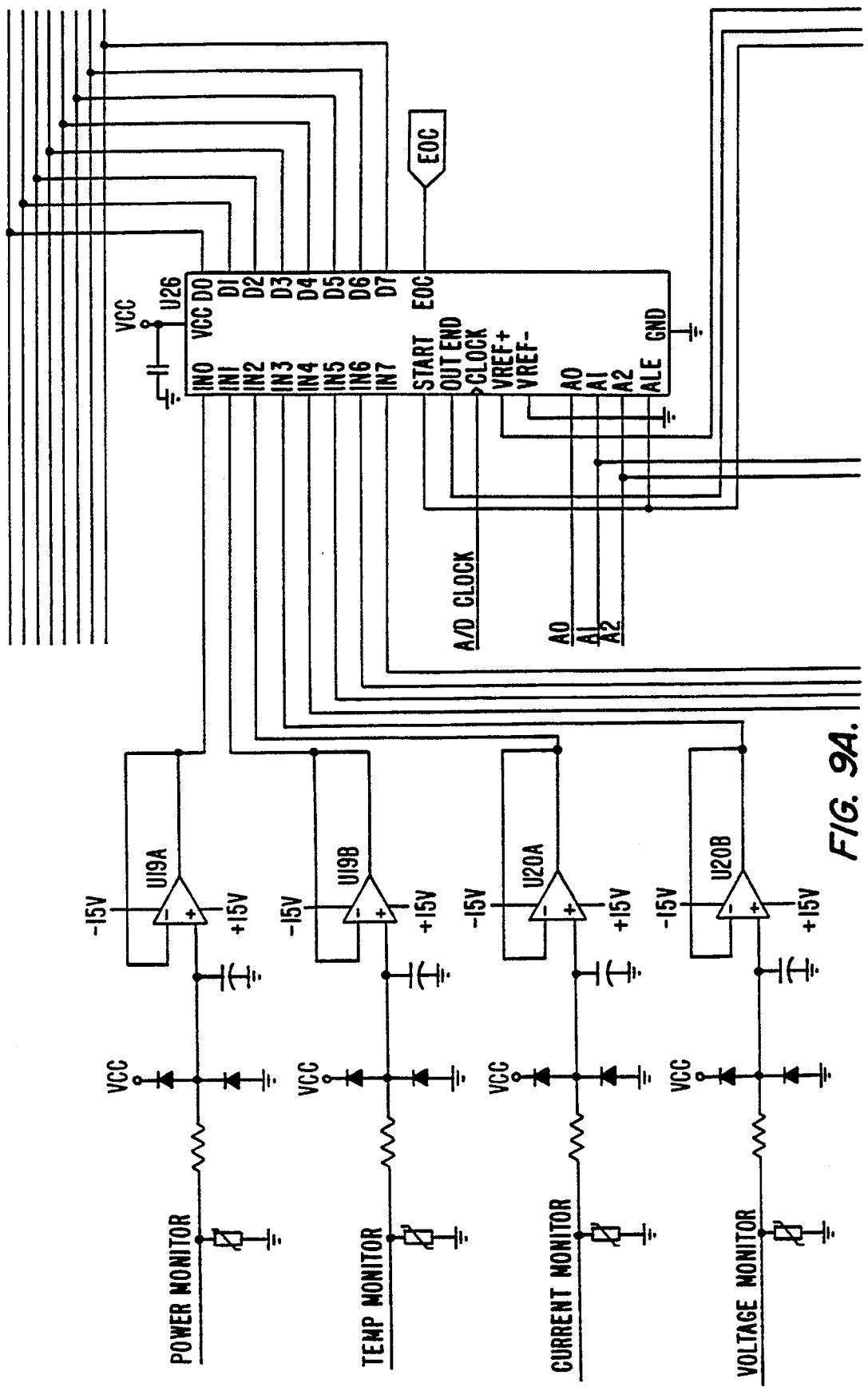
Figure 9B:
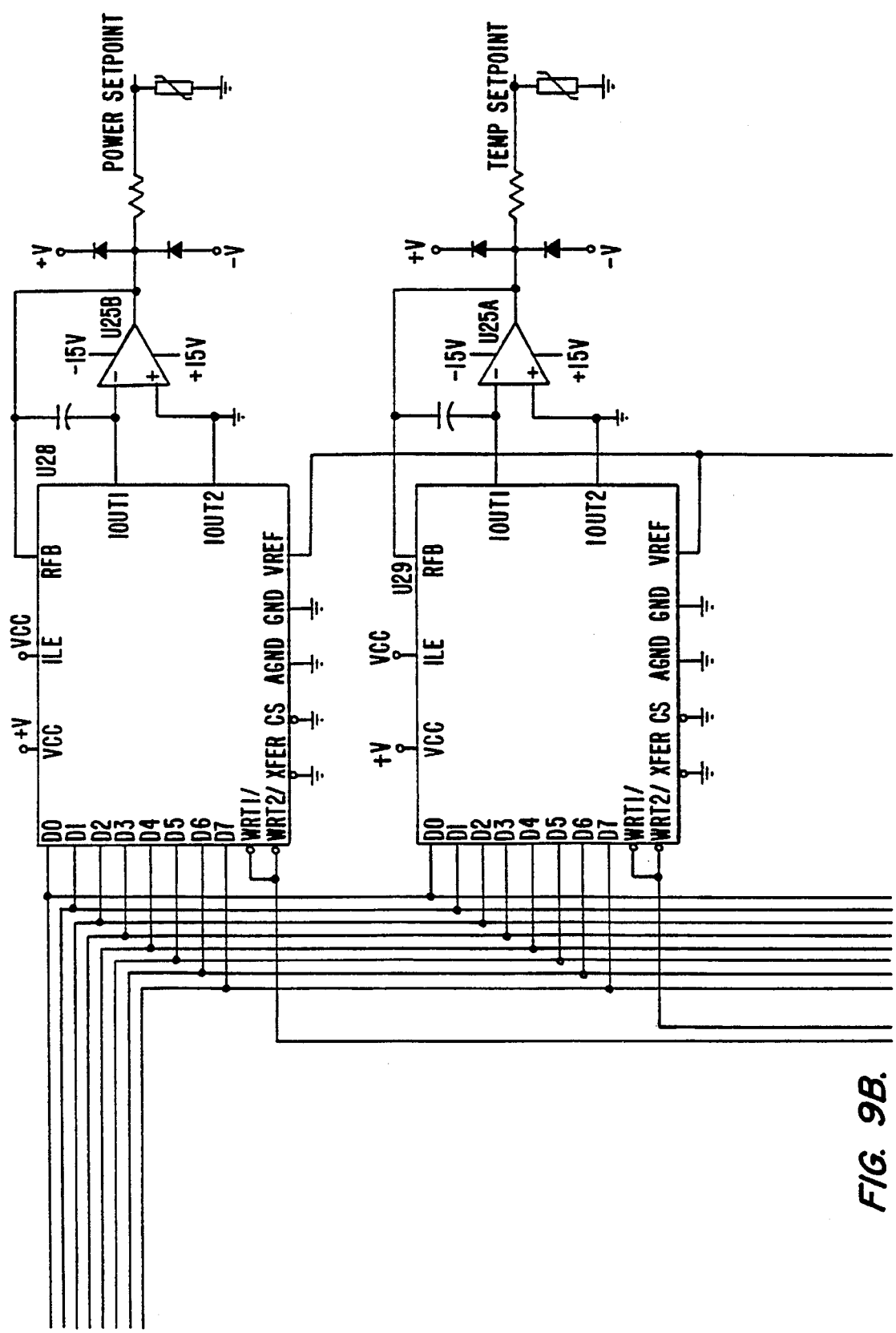
Figure 9D:
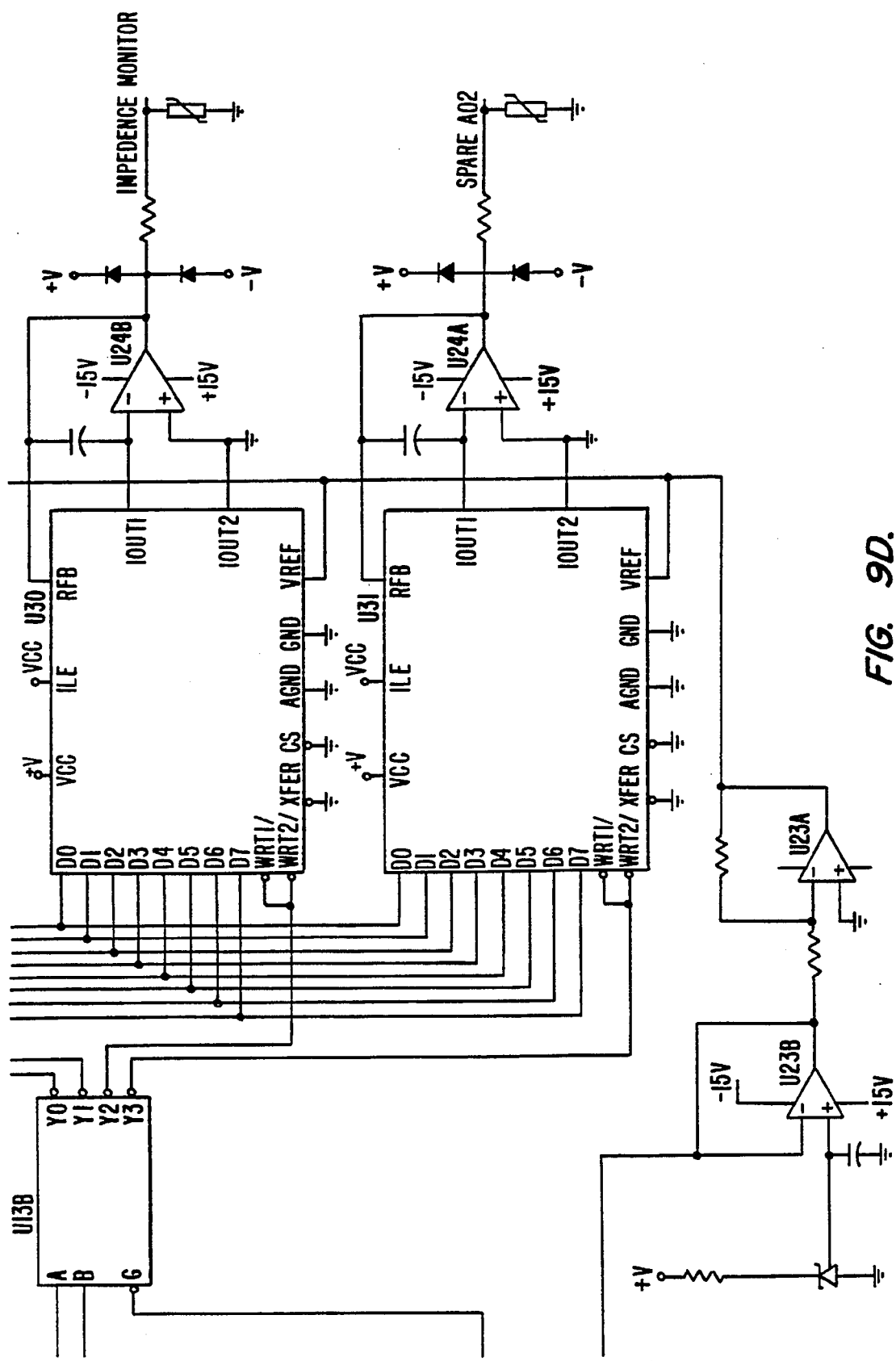
Figure 10A:
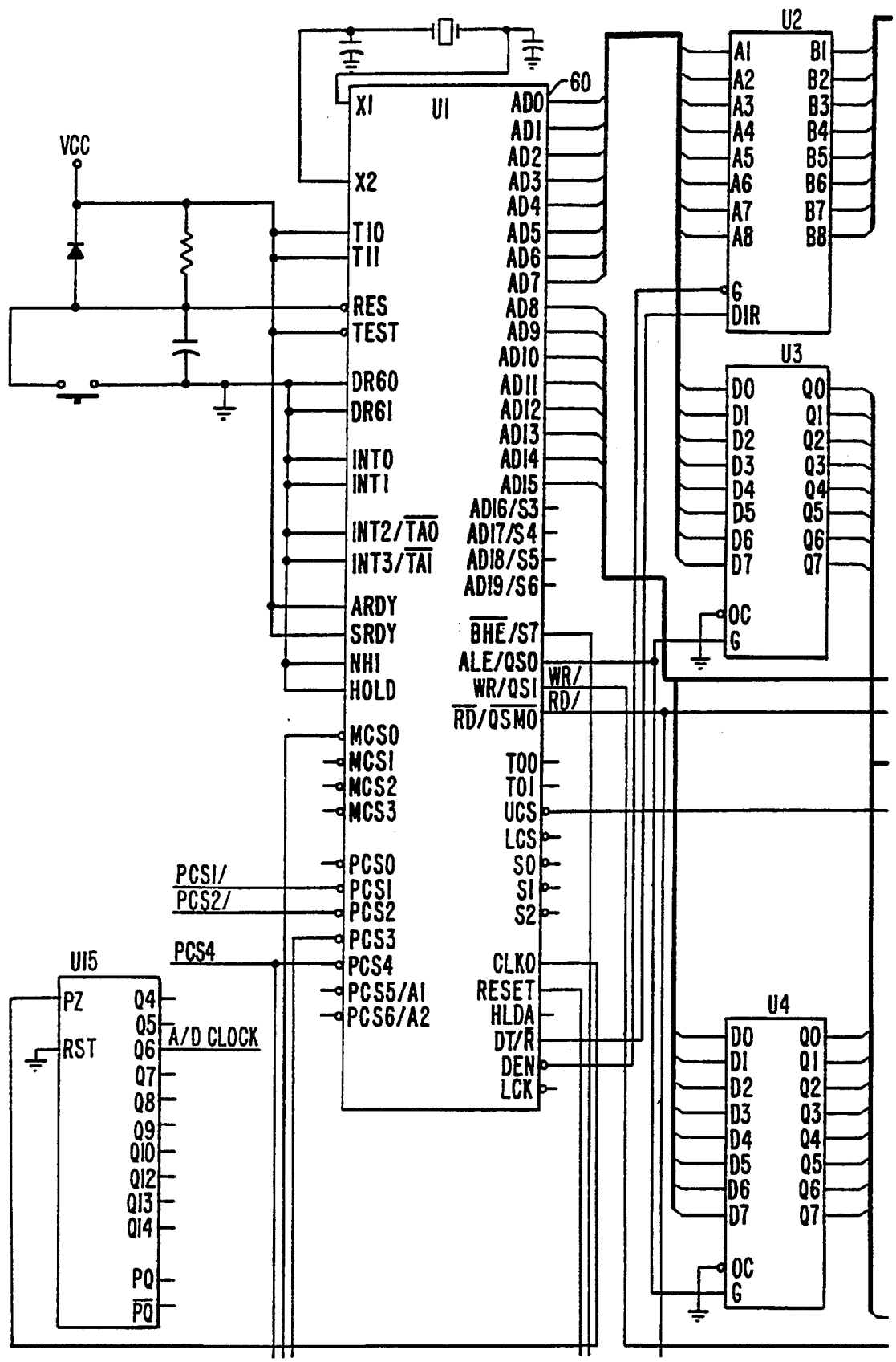
Figure 10B:
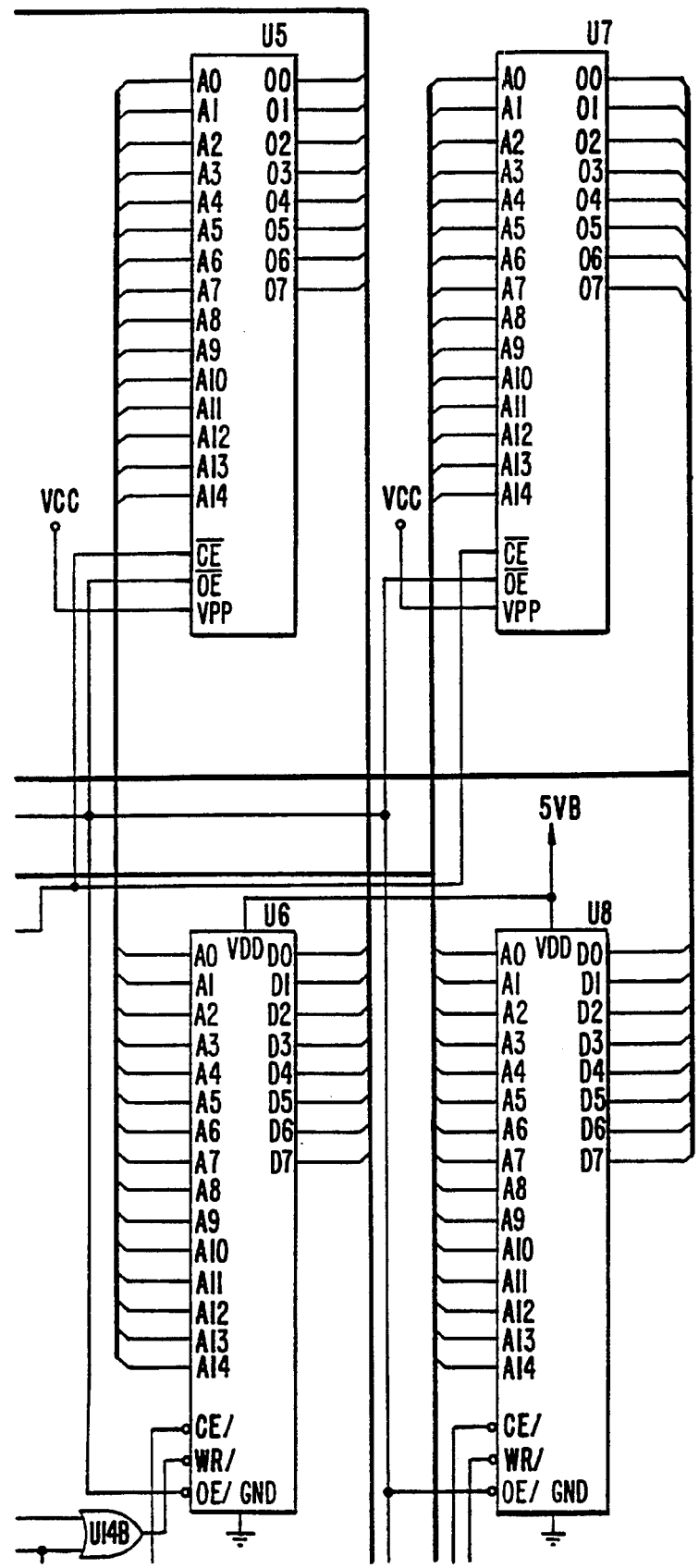
Figure 10C:
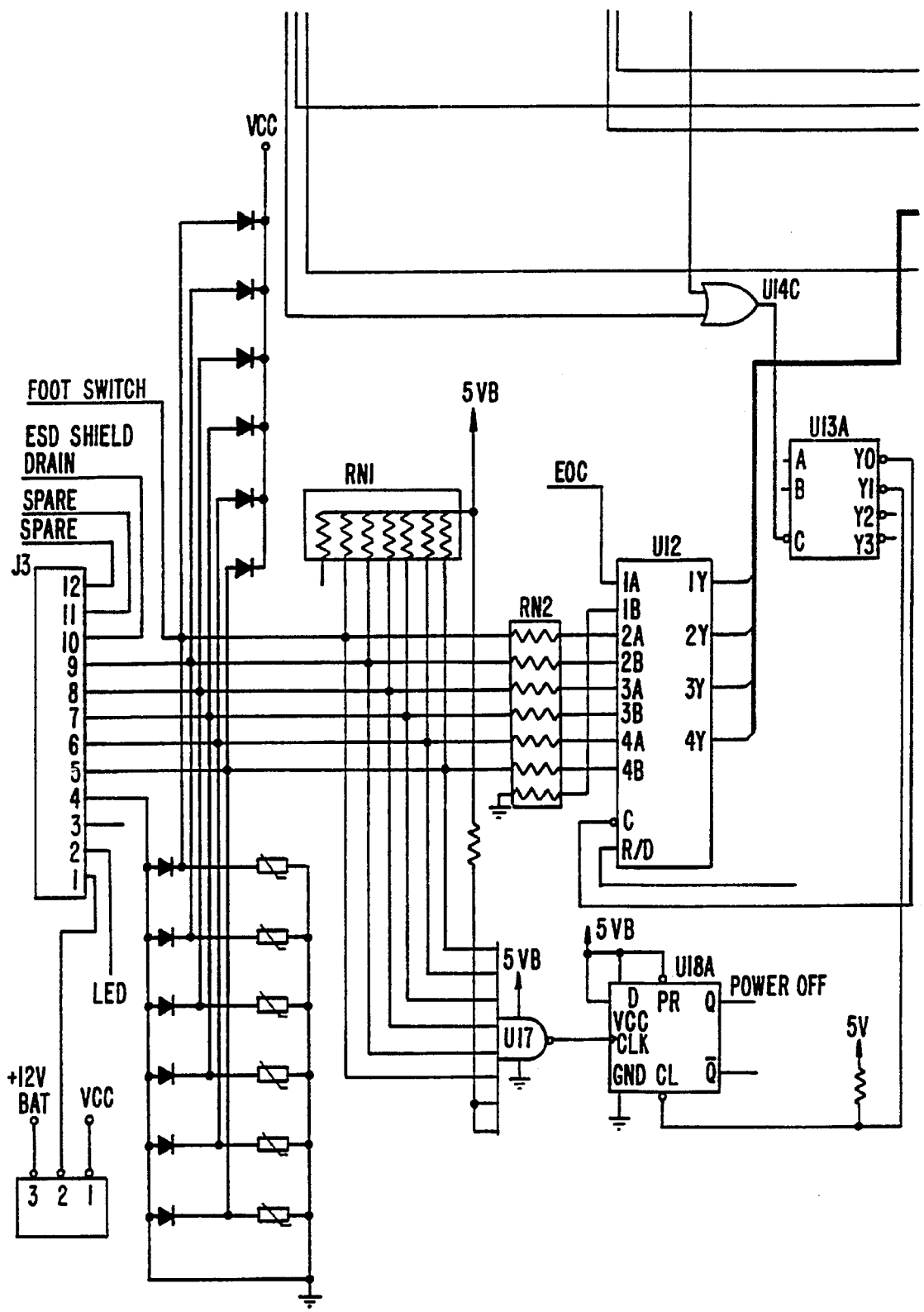
Figures 10, 10D:
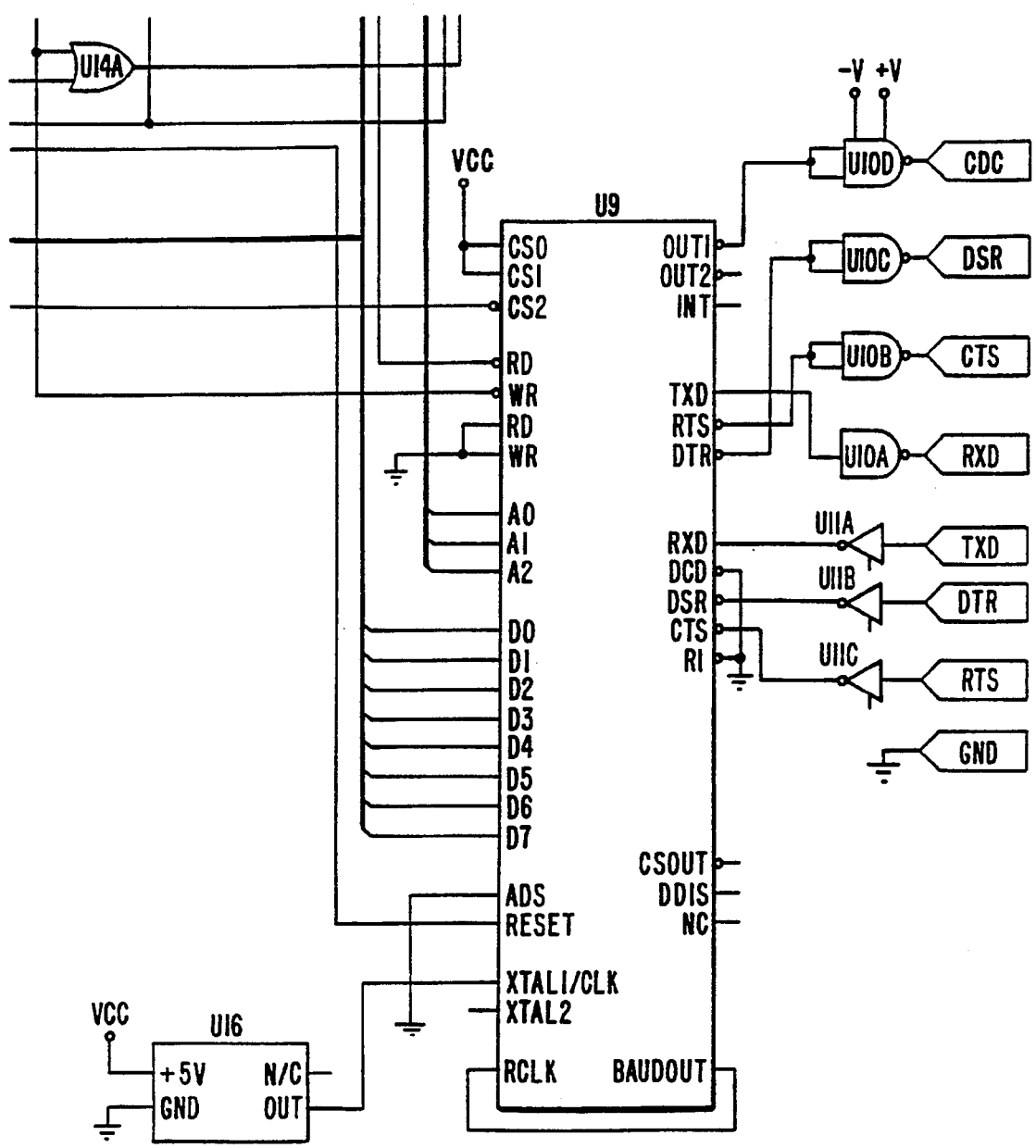
Figure 11B:
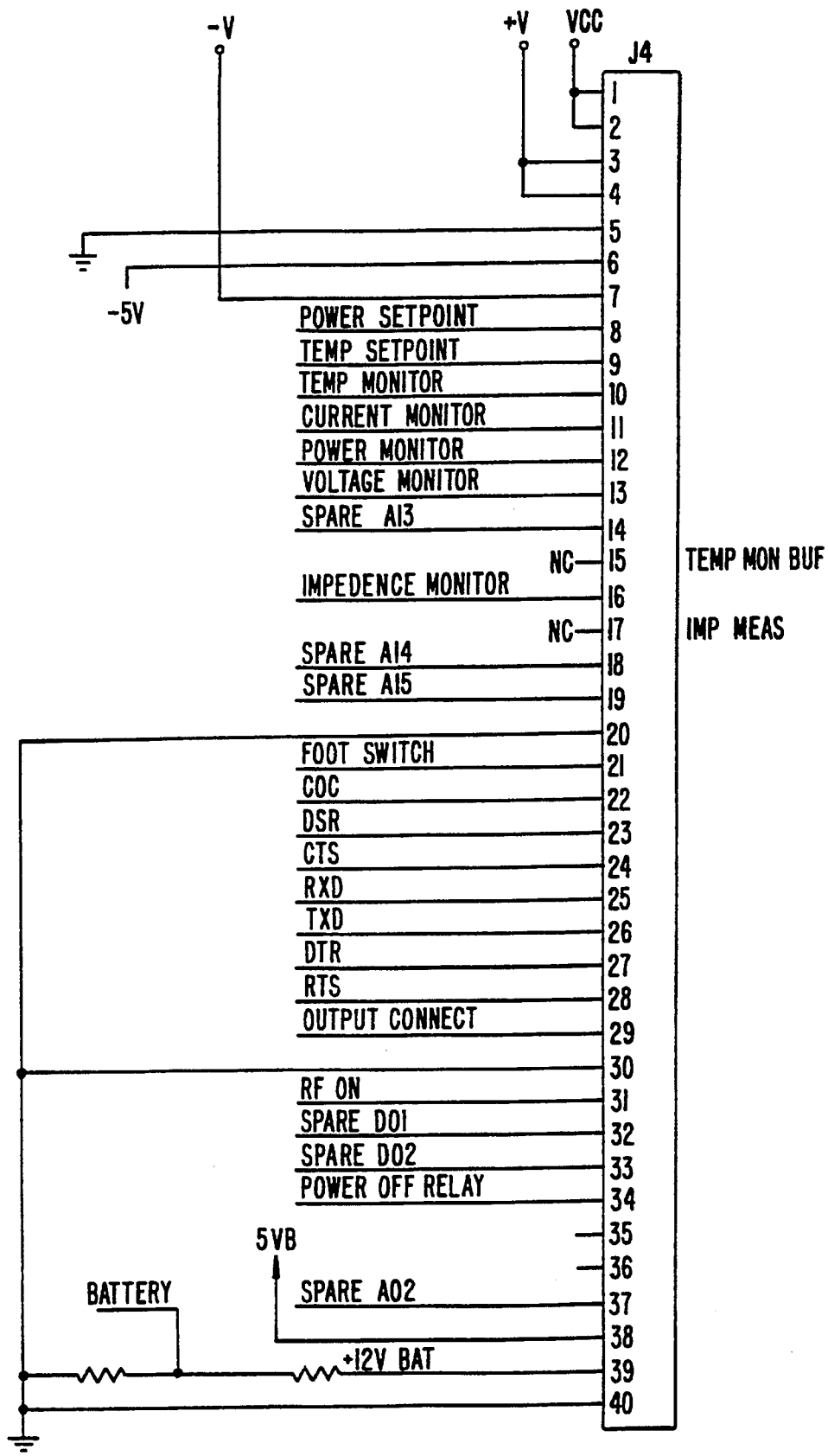
Figure 11C:
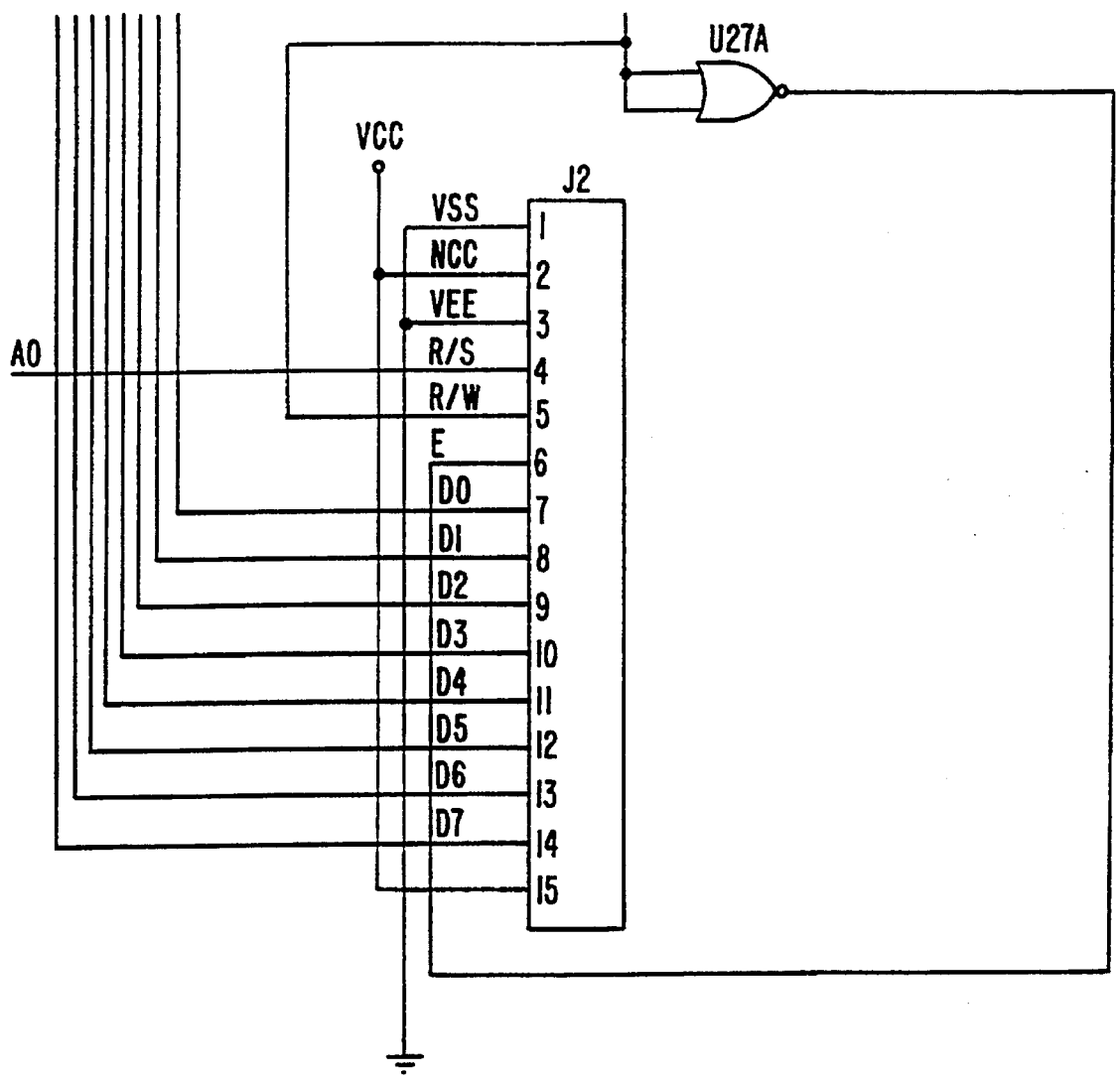
Figure 11:
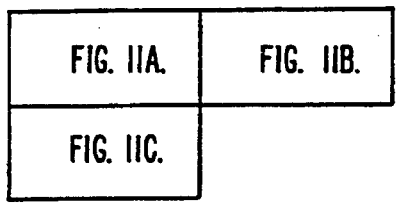

The microprocessor, operating via a 10 MHz clock, constantly monitors all function switches and zeros all DACs (inhibits any RF power command) in the event a malfunction is detected. The RF power generated by the unit cannot exceed 55 W. A comparator 94, shown in FIG. 7, shuts down RF power by limiting the duty cycle to final stage output transformer. Audible and visible alarms are provided in the following conditions: low battery; low/low battery prior to shut-down; low catheter impedance; high/low temperature; high power; and previously used catheter. The low impedance and a previously used catheter conditions inhibit any RF power command. In addition to the software controlled limits for temperature, power, and impedance (that turn off power if exceeded), there are also redundant hardware controls, including comparators 90, 96, that turn off power if the maximum temperature or power is exceeded.

In the preferred embodiment correct calibration of the thermocouple is checked prior to beginning ablation. The thermocouple output signal is provided as an input to the microprocessor 60 on line 85. Typically, the magnitude of this signal changes by known amount, for example about 20 mV/°C., at a particular temperature range. As described above, the analog inputs to the microprocessor 60 are converted to digital values.

When a user wishes to activate the RF power, the catheter has been in the body of the patient long enough that its temperature should be about equal to the body temperature of the patient, e.g., about 37° C.

Figure 13:
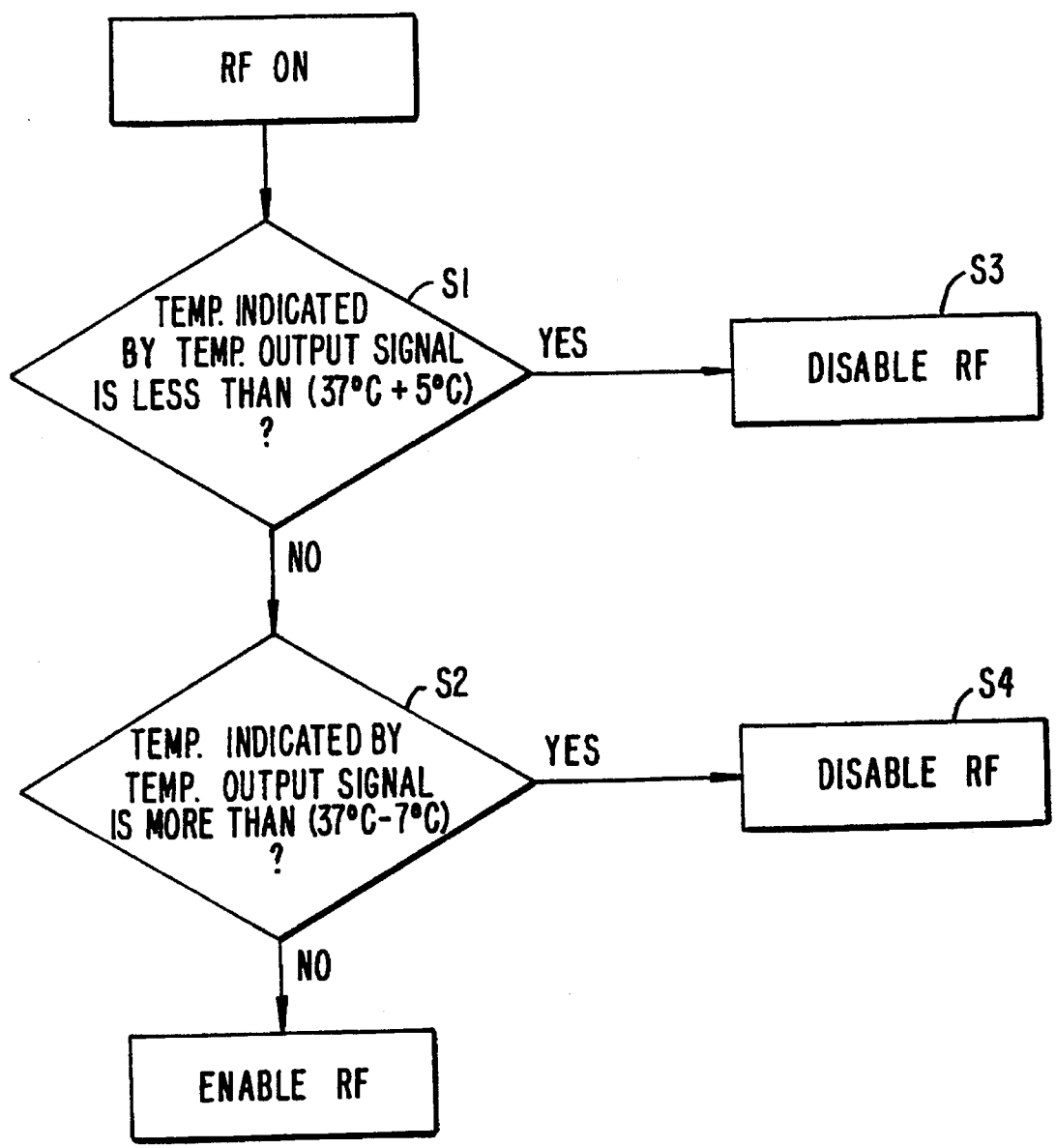
FIG. 13 is a flow chart depicting the steps of a pre-ablation themocouple calibration check.

The microprocessor 60 executes a software algorithm illustrated in FIG. 13 when the RF power is switched on. The magnitude of the thermocouple signal is compared to upper and lower limit temperatures (S1 and S2) to determine whether the temperature indicated is within a preselected range of 37° C. If not then the RF signal generator is disabled (S3 and S4) and if so then the RF generator is enabled and ablation is begun.

Use of the radiofrequency frequency ablation system 10 will begin by connecting the catheter 12 to the radiofrequency generator 18. After connection, the radiofrequency generator 18 will verify continuity to determine whether the thermocouple or other circuits are intact. This check is performed by delivering a low current signal through lines 22b to the thermocouple 30.

After introducing the catheter to the desired location within the patient's heart, the user will select the desired power delivery mode, i.e. power control or temperature control mode. Of particular interest to the present invention, the temperature control mode utilizes the cascade temperature control scheme described previously. The user selects the desired temperature set point and power is applied with the radiofrequency generator 18 precisely controlling the amount of power delivered in order to maintain the electrode temperature at the set point. Verification of the result of the treatment may be made using the ECG components of the catheter 12, or may be made using other conventional diagnostic techniques. Treatment may be repeated one or more times in order to achieve the desired ablation of the accessory pathway or location on the bundle of HIS.

Although the foregoing invention has been described in some detail by way of illustration and example, for purposes of clarity of understanding, it will be obvious that certain changes and modifications may be practiced within the scope of the appended claims. For example, although the initial calibration check of the thermocouple has been described as performed in software it is apparent that a hardware system could also be implemented. A reference voltage representing the expected magnitude of the signal could be provided to one input of a comparator and the thermocouple output to the other input. The comparator output would disable the RF power supply if the comparison indicated that the thermocouple was not properly functioning.

What is claimed is:

1. In a method for using a patient treatment device for insertion in the body of a patient that utilizes a temperature measuring device to control a procedure where a temperature output signal having a magnitude indicating the magnitude of the temperature is output by the temperature measuring device, the improvement comprising a method for preventing injury in the event that the temperature measuring device is incorrectly operating, said method for preventing comprising the steps of:

providing a reference value, stored in said device, having a magnitude of about 37° C. which indicates a normal body temperature of a patient;

comparing the temperature output signal to the reference value to determine whether the magnitude of the temperature output signal differs from the magnitude of the reference value by more that a predetermined amount;

disabling the patient treatment device if the magnitude of the temperature output signal differs from the magnitude of the reference value by more than a predetermined amount.

2. In a patient treatment device for insertion in the body of a patient that utilizes a temperature measuring device to control a procedure where a temperature output signal having a magnitude indicating the magnitude of the temperature is output by the temperature measuring device, the improvement comprising a system for preventing injury in the event that the temperature measuring device is incorrectly operating, said system comprising:

means for storing a reference value having a magnitude of about 37° C. which indicates a normal body temperature of a patient;

means, coupled to said means for storing and to receive said temperature output signal, for comparing the temperature output signal to the reference value to determine whether the magnitude of the temperature output signal differs from the magnitude of the reference value by more than a predetermined amount;

means, responsive to said means for comparing, for disabling the patient treatment device if the magnitude of the temperature output signal differs from the magnitude of the reference value by more than a predetermined amount.

3. In a patient treatment device for insertion in the body of a patient that utilizes a temperature measuring device to control a procedure, where a temperature output signal, having a magnitude indicating the magnitude of the actual body temperature of the patient, is output by the temperature measuring device, the improvement comprising a system for preventing injury in the event that the temperature measuring device is incorrectly operating, said system comprising:

a convertor for converting the magnitude of the temperature output signal to a digital temperature value;

a memory for storing a digital comparison value having a magnitude of about 37° C. which indicates the normal body temperature of a patient;

processor means, coupled to said convertor and said memory, for processing said digital temperature value and said digital comparison value to determine whether the magnitude of the temperature output signal indicates a temperature within a predetermined range of the normal body temperature of the patient and for disabling the patient treatment device if the indicated temperature is outside the predetermined range.

* * * * *